(12) United States Patent
Barth et al.

(10) Patent No.: US 6,794,382 B2
(45) Date of Patent: Sep. 21, 2004

(54) BENZIMIDAZOLE DERIVATIVES, PREPARATION AND THERAPEUTIC USE THEREOF

(75) Inventors: Francis Barth, Saint-Georges d'Oroues (FR); Daniel Bichon, Montpellier (FR); Frank Bolkenius, Kehl (DE); Viviane Van Dorsselaer, Strasbourg (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 10/343,467

(22) PCT Filed: Aug. 6, 2001

(86) PCT No.: PCT/FR01/02556

§ 371 (c)(1),
(2), (4) Date: Jan. 30, 2003

(87) PCT Pub. No.: WO02/12239

PCT Pub. Date: Feb. 14, 2002

(65) Prior Publication Data

US 2003/0203893 A1 Oct. 30, 2003

(30) Foreign Application Priority Data

Aug. 8, 2000 (FR) .............................. 00 10419
Nov. 15, 2000 (FR) .............................. 00 14696

(51) Int. Cl.[7] .................. C07D 471/06; C07D 487/06; A61K 31/4375; A61K 31/55; A61P 9/00
(52) U.S. Cl. ..................... 514/214.02; 514/217.05; 514/218; 514/253.03; 514/252.11; 514/275; 514/292; 540/575; 540/579; 540/598; 544/295; 544/361; 546/84
(58) Field of Search .............. 514/214.02, 217.05, 514/218, 253.03, 275, 252.11, 292; 540/575, 579, 598; 544/295, 361; 546/84

(56) References Cited

U.S. PATENT DOCUMENTS 5,589,476 A 12/1996 Jegham et al. ........... 514/230.2

FOREIGN PATENT DOCUMENTS

EP 0 646 583 A 4/1995
EP 0 732 334 A 9/1996
WO WO 00 32579 A 6/2000

*Primary Examiner*—Bruck Kifle
(74) *Attorney, Agent, or Firm*—Paul E. Dupont; Michael D. Alexander

(57) ABSTRACT

The invention relates to benzimidazole derivatives of general formula

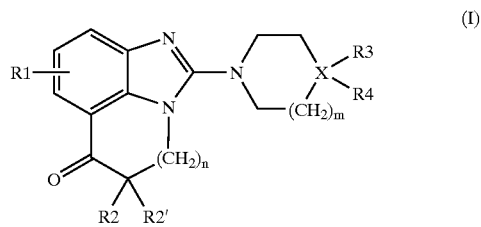

(I)

in which
X represents a nitrogen atom or a carbon atom;
and when X represents a nitrogen atom:
R3 represents a hydrogen atom or a C1–C4 alkyl group, or does not exist, to give the compounds of formula (I) comprising a secondary or tertiary amine;
R4 represents a hydrogen atom or a C1–C6 alkyl, C3–C7 cycloalkyl, optionally substituted C3–C7 heterocycloalkyl, —(CH$_2$)$_p$-heteroaryl, heteroaryl-carbonyl, phenylcarbonyl, (C1–C6) alkylcarbonyl, —(CH$_2$)$_p$COOR, optionally substituted phenylsulphonyl or optionally substituted —(CH$_2$)$_p$-phenyl group,
and, when X represents a carbon atom:
R3 represents a hydrogen atom or a group —NR5R6, —N(R5)$_3$$^+$, —NHCOR7, —CONHR5, —COR7, —NHCONH$_2$, —OH or —CH$_2$OH,
R4 represents a hydrogen atom or an optionally substituted —(CH$_2$)$_p$-phenyl, —(CH$_2$)$_p$-heteroaryl or —(CH$_2$)$_r$NR7R8 group.

Preparation process and therapeutic application.

25 Claims, No Drawings

BENZIMIDAZOLE DERIVATIVES, PREPARATION AND THERAPEUTIC USE THEREOF

The present invention relates to benzimidazole derivatives, to their preparation and to their therapeutic application.

The present invention relates to compounds corresponding to formula (I):

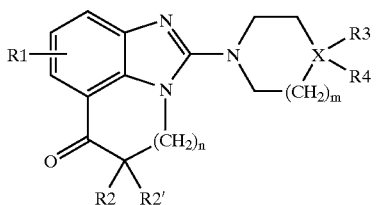

in which:
R1 represents a hydrogen atom, a C1–C4 alkyl group, a halogen atom, a nitro group or a C1–C4 alkoxy group,
R2 and R2' represent, independently of each other, a hydrogen atom or a C1–C4 alkyl group,
X represents a nitrogen atom or a carbon atom,
n is equal to 1 or 2,
m is equal to 1 or 2,
and, when X represents a nitrogen atom:
  R3 represents a hydrogen atom or a C1–C4 alkyl group, to give compounds of formula (I) comprising a quaternary ammonium, or alternatively does not exist, to give compounds of formula (I) comprising a secondary or tertiary amine,
  R4 represents
    a hydrogen atom,
    a C1–C6 alkyl group,
    a C3–C7 cycloalkyl group,
    a C3–C7 heterocycloalkyl group optionally substituted with a C1–C4 alkyl group or a group —COOR, in which R represents a C1–C6 alkyl group,
    a group —(CH$_2$)$_p$-heteroaryl, in which p may range from 0 to 4 and in which the heteroaryl group is chosen from pyridyl, aminopyridyl, pyrimidinyl, pyrazinyl, pyridazinyl, imidazolyl and thienyl groups, the said heteroaryl group optionally being substituted with a C1–C4 alkyl group,
    a heteroarylcarbonyl group, the heteroaryl group being chosen from furyl, pyridyl, pyrimidyl, pyrazinyl, pyridazinyl and imidazolyl groups,
    a phenylcarbonyl group, the phenyl group optionally being substituted with a halogen atom,
    a (C1–C6)alkylcarbonyl group,
    a group —(CH$_2$)$_p$COOR in which p may range from 0 to 4 and in which R represents a C1–C6 alkyl group,
    a phenylsulphonyl group optionally substituted on the phenyl nucleus with a halogen atom, a trifluoromethyl group, a C1–C4 alkyl group, a nitro group or a C1–C4 alkoxy group, or alternatively
    a —(CH$_2$)$_p$-phenyl group, in which p may range from 0 to 4 and in which the phenyl group is optionally substituted, in the ortho and/or meta and/or para position, with one to three groups chosen, independently of each other, from: a C1–C4 alkyl group, a nitro group, an amino group, a hydroxyl group, a halogen atom, a trifluoromethyl group, a C1–C4 alkoxy group, a (C1–C4)alkoxyphenyl group, a C1–C4 alkylamino group, a C1–C4 dialkylamino group, an —NHCHO group or a group —NHCOR', in which R' represents a C1–C4 alkoxy group or a C1–C4 alkyl group, this C1–C4 alkyl group optionally being substituted with a dimethylamino group,
and, when X represents a carbon atom:
  R3 represents a hydrogen atom, a group —NR5R6, a group —N(R5)$_3$$^+$, a group —NHCOR7, a group —CONHR5, a group —COR7, an —NHCONH$_2$ group, an —OH group or a —CH$_2$OH group,
  R4 represents
    a hydrogen atom,
    a —(CH$_2$)$_p$-phenyl group, in which p may range from 0 to 4 and in which the phenyl group is optionally substituted with one to three groups chosen, independently of each other, from: a C1–C4 alkyl group, a nitro group, an amino group, a halogen atom, a trifluoromethyl group or a C1–C4 alkoxy group,
    a —(CH$_2$)$_p$-heteroaryl group, in which p may range from 0 to 4 and in which the heteroaryl group is chosen from an imidazolyl group, optionally substituted with a C1–C4 alkyl group, a pyridyl group, an aminopyridyl group, a pyrimidinyl group, a pyrazinyl group or a pyridazinyl group, or alternatively
    a group —(CH$_2$)$_t$NR7R8, in which t is equal to 0 or 1,
    with the proviso that when R4 represents a group —NR7R8, R3 is other than the groups —NR5R6, —NHCOR7, —NHCONH$_2$ and —OH,
  R5 and R6 represent, independently of each other, a hydrogen atom or a C1–C4 alkyl group,
  R7 and R8 represent, independently of each other, a C1–C4 alkyl or C1–C4 alkoxy group or together form a saturated 5- to 7-membered ring optionally comprising an additional nitrogen atom, to form, for example, a 1-piperidyl group, a 1-pyrrolidinyl group or a 1-piperazinyl group, this ring optionally being substituted, on a carbon atom or on a nitrogen atom, including the nitrogen atom to which the groups R7 and R8 are attached to form a quaternary ammonium, with a C1–C4 alkyl group or a group —COOR", in which R" represents a phenyl or (C1–C4)alkylphenyl group,
with the exclusion of the two compounds for which R1=R2=R2'=R3=H, X=C, n=m=1 and R4 represents either a 4-imidazolyl group or a 5-methyl-4-imidazolyl group.

These two compounds are disclosed in patent application EP 646 583, as compounds 16 and 17 in the table, as 5-HT$_3$ and 5-HT$_4$ type serotoninergic receptor ligands.

The compounds of formula (I) may comprise one or more asymmetric carbon atoms. They may thus exist in the form of enantiomers or diastereoisomers. These enantiomers and diastereoisomers, and also the mixtures thereof, including racemic mixtures, form part of the invention.

The compounds of the invention may exist in the form of bases or of addition salts with pharmaceutically acceptable acids. Such addition salts also form part of the invention.

In the context of the present invention, the term:

"a (Cq-Cr)alkyl group" means a linear or branched saturated aliphatic group comprising from q to r carbon atoms, q and r being integers; mention may be made in particular of methyl, ethyl, propyl, isopropyl, n-propyl, butyl, isobutyl, tert-butyl, n-butyl, pentyl, etc. groups;

"a halogen atom" means a fluorine, a chlorine, a bromine or an iodine;

"a C3–C7 cycloalkyl group" means a cyclic alkyl group containing from 3 to 7 carbon atoms; mention may be made in particular of cyclopropyl, cyclobutyl, cyclopentyl, cyclohexyl and cycloheptyl groups;

"a C3–C7 heterocycloalkyl group" means a cyclic alkyl group containing from 3 to 7 carbon atoms and also one or more hetero atoms, for example a nitrogen atom; mention may be made in particular of piperidyl groups;

"a (C1–C4)alkoxyphenyl group" means a group of formula —O—$(CH_2)_x$-phenyl, in which x may range from 1 to 4.

Among the compounds of formula (I) which are the subjects of the present invention, mention may be made of the preferred compounds for which:

R1 represents a hydrogen atom, a C1–C4 alkyl group or a C1–C4 alkoxy group,

R2 represents a hydrogen atom or a C1–C4 alkyl group,

R2' represents a hydrogen atom,

X represents a nitrogen atom, n is equal to 1 or 2, m is equal to 1 or 2,

R3 represents a hydrogen atom, to give compounds of formula (I) comprising a quaternary ammonium, or alternatively does not exist, to give compounds of formula (I) comprising a secondary or tertiary amine, R4 represents
  a hydrogen atom,
  a C1–C6 alkyl group,
  a C3–C7 cycloalkyl group,
  a pyridyl, pyrimidinyl or pyrazinyl group, optionally substituted with a C1–C4 alkyl group,
  a heteroarylcarbonyl group, the heteroaryl group being chosen from a furyl group and a pyridyl group,
  a phenylcarbonyl group, the phenyl group optionally being substituted with a halogen atom,
  a (C1–C6)alkylcarbonyl group,
  a group —$(CH_2)_p$COOR in which p can range from 0 to 4 and in which R represents a C1–C6 alkyl group,
  a phenylsulphonyl group,
  a phenyl group substituted with one to three groups chosen, independently of each other, from: a C1–C4 alkyl group, a nitro group, an amino group, a hydroxyl group, a halogen atom, a trifluoromethyl group, a C1–C4 alkoxy group, a (C1–C4) alkoxyphenyl group, a (C1–C4)dialkylamino group, an —NHCHO group or a group —NHCOR', in which R' represents a C1–C4 alkoxy group or a C1–C4 alkyl group, this C1–C4 alkyl group optionally being substituted with a dimethylamino group,
  a —$(CH_2)_p$-phenyl group, in which p can range from 0 to 4,
  a —$(CH_2)_p$-pyridyl group, in which p can range from 0 to 4,
  a —$(CH_2)_p$-thienyl group, in which p can range from 0 to 4,
  a (C3–C7)heterocycloalkyl group optionally substituted with a C1–C4 alkyl group or a group —COOR, in which R represents a C1–C6 alkyl group, or alternatively the preferred compounds for which:

R1 represents a hydrogen atom,

R2 and R2' represent, independently of each other, a hydrogen atom or a C1–C4 alkyl group, X represents a carbon atom, n is equal to 1 or 2, m is equal to 1, R3 represents a hydrogen atom, a group —NR5R6, a group —$N(R5)_3^+$, a group —NHCOR7, a group —CONHR5, an —$NHCONH_2$ group, an —OH group or a —$CH_2OH$ group, R4 represents
  a hydrogen atom,
  a benzyl group (namely a —$(CH_2)_p$-phenyl group in which p is equal to 1),
  a phenyl group optionally substituted with one to three groups chosen, independently of each other, from: a C1–C4 alkyl group, a nitro group, an amino group, a halogen atom, a trifluoromethyl group or a C1–C4 alkoxy group,
  a heteroaryl group chosen from an imidazolyl group, optionally substituted with a C1–C4 alkyl group, or a pyridyl group,
  a group —NR7R8,
with the proviso that when R4 represents a group —NR7R8, R3 is other than the groups —NR5R6, —NHCOR7, —$NHCONH_2$ and —OH, R5 and R6 represent, independently of each other, a hydrogen atom or a C1–C4 alkyl group, R7 and R8 represent, independently of each other, a C1–C4 alkyl or C1–C4 alkoxy group, or together form a saturated 5- to 7-membered ring optionally comprising an additional nitrogen atom, this ring optionally being substituted, on a carbon atom or a nitrogen atom, including the nitrogen atom to which the groups R7 and R8 are attached to form a quaternary ammonium, with a C1–C4 alkyl group or a group —COOR", in which R" represents a phenyl or (C1–C4)alkylphenyl group, with the exclusion of the two compounds for which R1=R2=R2'=R3=H, X=C, n=m=1 and R4 represents either a 4-imidazolyl group or a 5-methyl-4-imidazolyl group.

Among the latter preferred compounds, ones most particularly preferred are the compounds of formula (I) for which:

R1 represents a hydrogen atom, a methyl group or a methoxy group,

R2 represents a hydrogen atom or a methyl group,

R2' represents a hydrogen atom,

X represents a nitrogen atom, n is equal to 1 or 2, m is equal to 1 or 2,

R3 represents a hydrogen atom, to give compounds of formula (I) comprising a quaternary ammonium, or alternatively does not exist, to give compounds of formula (I) comprising a secondary or tertiary amine, R4 represents
  a hydrogen atom,
  a C1–C4 alkyl group,
  a C6–C7 cycloalkyl group,
  a pyridyl, pyrimidinyl or pyrazinyl group, optionally substituted with a C1–C4 alkyl group,
  a heteroarylcarbonyl group, the heteroaryl group being chosen from a furyl group and a pyridyl group, a phenylcarbonyl group, the phenyl group optionally being substituted with a halogen atom, a (C3–C5)alkylcarbonyl group, a group —(CH$_2$)$_p$COOR in which p is equal to 0 or 1 and in which R represents a C1–C4 alkyl group, a phenylsulphonyl group, a phenyl group substituted with one to three groups chosen, independently of each other, from: a methyl group, a nitro group, an amino group, a hydroxyl group, a halogen atom, a trifluoromethyl group, a methoxy group, a (C1–C4)alkoxyphenyl group, a dimethylamino group, an —NHCHO group or a group —NHCOR', in which R' represents a C1–C4 alkoxy group or a C1–C4 alkyl group, this C1–C4 alkyl group optionally being substituted with a dimethylamino group, a —(CH$_2$)$_p$-phenyl group, in which p is equal to 1, 2, 3 or 4, a —(CH$_2$)$_p$-pyridyl group, in which p can range from 1 to 3, a —(CH$_2$)$_p$-thienyl group, in which p is equal to 2, a C6–C7 heterocycloalkyl group optionally substituted with a methyl group or a group —COOR, in which R represents a C1–C4 alkyl group, or alternatively, the compounds that are most particularly preferred are those of formula (I) for which:

R1 represents a hydrogen atom,

R2 and R2' represent, independently of each other, a hydrogen atom or a methyl group, X represents a carbon atom, n is equal to 1 or 2, m is equal to 1, R3 represents a hydrogen atom, a group —NR5R6, an —N(CH$_3$)$_3^+$ group, a group —NHCOR7, a group —CONHR5, an —NHCONH$_2$ group, an —OH group or a —CH$_2$OH group, R4 represents
   a hydrogen atom,
   a benzyl group,
   a phenyl group optionally substituted with one to three groups chosen, independently of each other, from a halogen atom and a trifluoromethyl group, a heteroaryl group chosen from an imidazolyl group, optionally substituted with a methyl group, or a pyridyl group, a group —NR7R8, with the proviso that when R4 represents a group —NR7R8, R3 is other than the groups —NR5R6, —NHCOR7, —NHCONH$_2$ and —OH, R5 and R6 represent, independently of each other, a hydrogen atom or a C1–C4 alkyl group, R7 and R8 represent, independently of each other, a C1–C4 alkyl group or together form a saturated 5- to 7-membered ring optionally comprising an additional nitrogen atom, this ring optionally being substituted, on a carbon atom or on a nitrogen atom, including the nitrogen atom to which the groups R7 and R8 are attached to form a quaternary ammonium, with a methyl group or a group —COOR", in which R" represents a (C1–C4)alkylphenyl group, with the exclusion of the two compounds for which R1=R2=R2'=R3=H, X=C, n=m=1 and R4 represents either a 4-imidazolyl group or a 5-methyl-4-imidazolyl group.

In the text hereinbelow, the term "leaving group" means a group which may be readily cleaved from a molecule by heterolytic cleavage of a bond, with departure of an electron pair. This group may thus be readily replaced with another group during, for example, a substitution reaction. Such leaving groups are, for example, halogens or an activated hydroxyl group such as a mesyl, tosyl, triflate, acetyl, etc. Examples of leaving groups and references for preparing them are given in "Advances in Organic Chemistry", J. March 3rd Edition, Wiley Interscience pp. 310–316.

To prepare the compounds of formula (I) in accordance with the invention, the process is performed according to the synthetic scheme 1 below. According to this process, a derivative of formula (II), in which R1, R2, R2' and n are as defined above and A represents a leaving group, preferably a halogen, are reacted in the presence of an amine of formula (III), in which X, R3, R4 and m are as defined above, in a solvent which may be an alcohol, such as isoamyl alcohol, an ether such as tetrahydrofuran or TGME (triethylene glycol monomethyl ether) or a hydrocarbon such as toluene, at a temperature of between room temperature and the boiling point of the solvent, to give the compound of formula (I). The reaction may be carried out in the presence of a base such as 2,6-dimethyllutidine or sodium tert-butoxide, in the presence of alkali metal halides such as potassium fluoride or in the presence of palladium-based or nickel-based catalysts, as described, for example, in patent application EP 646 583 or in *J. Med. Chem.* (1986) 29 1178–1183, *Tetrahedron Letters* (1997) 32 5607–5610, *Tetrahedron Letters* (1999) 55 12829–12842 and *Tetrahedron Letters* (1999) 40 6875–6879.

When the compound of formula (I) comprises a free primary or secondary amine function, it may also be obtained by reacting a derivative of formula (II) with an amine of formula (III) in which the said amine function is protected with a conventional amine-protecting group such as a tert-butyl carbamate (BOC). The compound of formula (I) containing a protected amine function, thus obtained, is then treated according to one of the known methods to give the desired compound (I) containing a free amine function. Examples of amine-protecting groups and of deprotection methods are given in particular in T. W. Greene, P. G. M. Wuts, "Protective Groups in Organic Synthesis", J. Wiley, Ed., 1991.

Scheme 1:

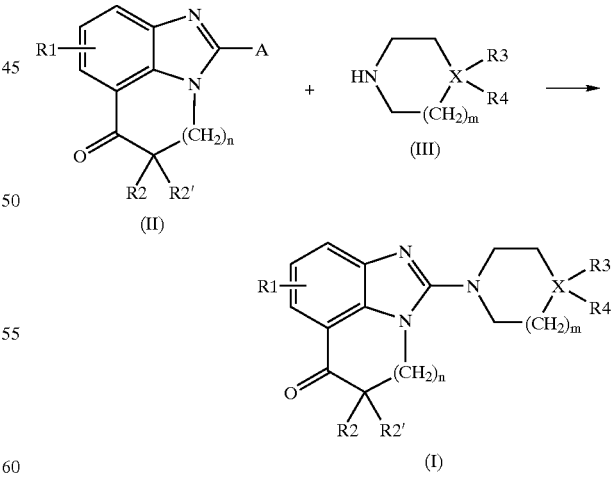

The compounds of formula (II) may be prepared according to Scheme 2 below, according to operating conditions that are known to those skilled in the art, in particular by reacting a compound of formula (IV), in which R1, R2, n and R2' are as defined above, with a halogenating agent such as phosphoryl chloride.

Scheme 2:

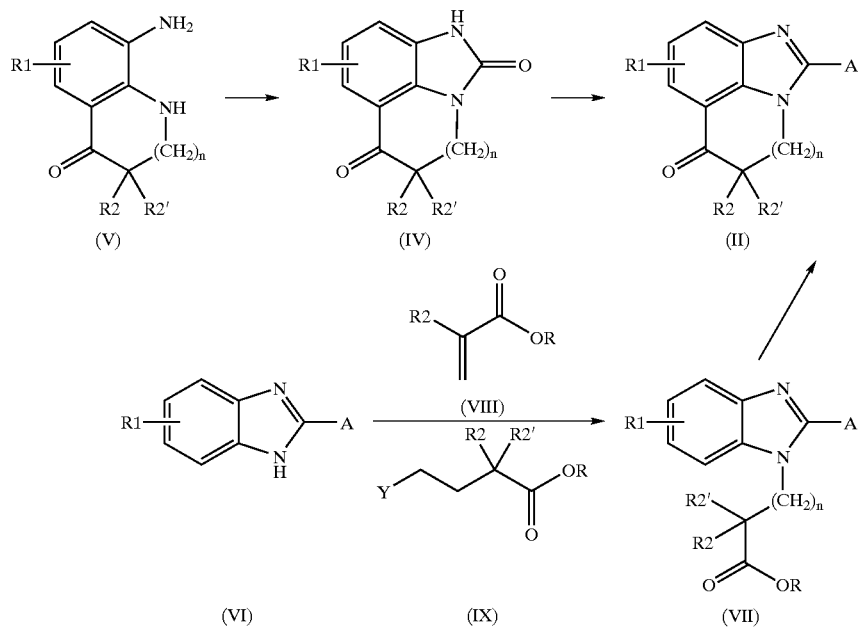

The compounds of formula (IV) may be prepared according to a process described in synthetic scheme 2 above. According to one variant of this process, a diamine of formula (V), in which R1, R2, R2' and n are as defined above, is coupled with a phosgene derivative such as carbonyldiimidazole (CDI). According to another variant, a derivative of formula (VI), in which R1 is as defined above, is alkylated with an alkylating agent of formula (VIII), R=C1–C4 alkyl) in which R2 is as defined above, to give the products of formula (VII) in which n=1 and R2'=H, or with an agent of formula (IX, R=C1–C4 alkyl) and Y is a leaving group, in which R2 and R2' are as defined above, to give the products of formula (VII) in which n=2. The compounds (VII) thus obtained are then converted into carboxylic acids (VII, R=H) or into acid derivatives such as acid chlorides (VII, R=Cl) and then cyclized under operating conditions known to those skilled in the art, to give the intermediates of formula (II) directly. An approach similar to this second variant is described in particular in patent application JP 55111406 or in *Tetrahedron Letters* (1995) 36 1387–1390.

Alternatively, the compounds of formula (II) in which R2 and R2' do not represent hydrogen atoms may be prepared from the corresponding compounds (II) in which R2' represents a hydrogen atom, by alkylation with a reagent of the type R2' Z in which Z represents a leaving group, preferably iodine. This reaction may be carried out in a solvent such as dimethylformamide, ether or tetrahydrofuran in the presence of a base, according to methods known to those skilled in the art.

The compounds of formulae (III), (V), (VI), (VIII) and (IX) are commercially available or may be prepared according to operating conditions that are known to those skilled in the art.

A subject of the present invention is also the novel synthetic intermediates of formula (II).

The examples which follow illustrate the present invention. The numbers for the compounds given as examples refer to those in the table given later, which illustrates the chemical structures of a number of compounds according to the invention.

EXAMPLE 1

Preparation of Intermediates of Formula (II)

1.1 Preparation of 2-chloro-4,5-dihydro-imidazo[4,5,1-ij]quinolin--6-one (A=Cl, R1=H, R2=R2'=H, n=1)

This compound is obtained from the compound 4H-imidazo[4,5,1-ij]quinolin-2,6-(1H,5H)dione (IV), described in Japanese patent: JP 55111406. 10 g of compound (IV) are reacted at reflux with 38.6 mL of phosphorous oxychloride and 6.3 g of ammonium chloride, for 1.5 hours, in a 250 mL three-necked flask fitted with a reflux condenser. The reaction mixture is then cooled and poured onto ice, to which is added 20% aqueous ammonia solution with vigorous stirring, until a pH of 9 is obtained. The mixture is extracted with twice 250 mL of ethyl acetate, dried over magnesium sulphate, filtered and evaporated. 9.81 g of a white solid are obtained and are used without further purification in the following step. $^1$H NMR (200 MHz, δ ppm) DMSO D6: 7.8 (d, 1H), 7.5 (d, 1H), 7.3 (t, 1H), 4.5 (t, 2H), 3.0 (t, 2H).

1.2 Preparation of 1-chloro-8,9-dihydro-7H-2,9a-diazabenzo[cd]azulen-6-one (A=Cl, R1=H, R2=R2'=H, n=2)

1.2.1: Ethyl 3-(2-chlorobenzimidazol-1-yl)butyrate Sodium hydride as a 60% dispersion in oil (2.88 g, 72 mmol) is introduced, under a nitrogen atmosphere, into a 1 L three-necked flask with a magnetic stirrer, an addition funnel and a condenser, the sodium hydride is washed twice with pentane and a small amount of dimethylformamide is added, followed by a solution of ethyl 4-bromobutyrate (14.78 g, 72 mmol) in anhydrous dimethylformamide (200 mL). After stirring for one hour at room temperature, 2-chloro-1H-benzimidazole (10.0 g, 65.5 mmol) dissolved in anhydrous dimethylformamide (200 mL) is added to the mixture. The reaction mixture is heated at 65° C. for 8 hours and is then kept at room temperature overnight. After evaporation of the dimethylformamide, the residue is taken up in ethyl acetate and the organic phase is washed with saturated sodium chloride, dried over magnesium sulphate, filtered and concentrated. A flash chromatography on silica gel (750 g) of the crude product (22 g) with an elution gradient of from 10% to 30% ethyl acetate in petroleum ether gives the title compound in the form of a yellow oil (16.58 g, 95%). $^1$H NMR (300 MHz, δ ppm) CDCl$_3$: 1.25 (t, 3H), 2.15 (quint., 2H), 2.40 (t, 2H), 4.15 (quartet, 2H), 4.25, (t, 2H), 7.20–7.40 (m, 2H), 7.70 (dd, 1H).

1.2.2: Lithium 3-(2-chloro-1-benzimidazolyl)butoxide

The ethyl ester (16.58 g, 62.2 mmol) dissolved in tetrahydrofuran (180 mL) is introduced into a 1 L one-necked round-bottomed flask with magnetic stirring, followed by addition of aqueous lithium hydroxide solution (1.49 g, 24 mmol, 100 mL of distilled water). The mixture is left to react overnight at room temperature, the tetrahydrofuran and water are evaporated off and the residue is then taken up in ethyl ether (2 L) and stirred for 2 hours. The white precipitate obtained is filtered off, washed with ethyl ether and then dried thoroughly under vane-pump vacuum over phosphorous pentoxide to give the expected compound in the form of white crystals (14 g, 92%). The compound is used without further purification for the following step. $^1$H NMR (300 MHz, δ ppm) DMSO D6+ε D$_2$O: 1.85 (m, 2H), 1.95 (m, 2H), 4.20 (t, 2H), 7.25 (m, 2H), 7.55 (d, 1H), 7.60 (d, 1H). LC-MS: MH$^+$=239 (acid).

1.2.3: 1-Chloro-8,9-dihydro-7H-2,9a-diazabenzo[cd]-azulen-6-one

The lithium salt (11.95 g, 49.7 mmol) is introduced into a 2 L three-necked flask under an argon atmosphere, with magnetic stirring, a condenser and an addition funnel, followed by addition of 1,2-dichloroethane freshly distilled over phosphorous pentoxide (1 L). Oxalyl chloride (8.55 mL, 102 mmol) is added quickly with stirring and the reaction mixture is heated for 15 min at about 40° C. Aluminium chloride (19.54 g, 154.5 mmol) is added to the intermediate acid chloride thus obtained and the mixture is refluxed for 3 hours. The resulting mixture is cooled and then poured onto an ice/salt mixture and extracted with 1,2-dichloroethane, the organic phase is washed with saturated sodium chloride solution, dried over magnesium sulphate and filtered and the solvent is then evaporated off. A flash chromatography of the crude product (10.6 g) on silica gel (800 g), eluting with 20% ethyl acetate in dichloromethane, gives the expected product in the form of white crystals (7.06 g, 65%). $^1$H NMR (300 MHz, δ ppm) CDCl$_3$: 2.40 (quint., 2H), 3.15 (t, 2H), 4.40, (t, 2H), 7.35 (t, 1H), 7.95 (d, 1H), 8.05 (d, 1H). LC-MS: MH$^+$=221.

1.3 Preparation of 2-chloro-5-methyl-4,5-dihydroimidazo[4,5,1-ij]quinolin-6-one (A=Cl, R1=H, R2=CH$_3$, R2'=H, n=1)

1.3.1: Methyl 1-methyl-3-(2-chloro-1-benzimidazol-yl) propionate

2-Chloro-1H-benzimidazole (15.25 g, 100 mmol) dissolved in chloroform (100 mL) is introduced into a 1 L three-necked flask under a nitrogen atmosphere, with magnetic stirring, an addition funnel and a condenser. Triton B (47 mL, 110 mmol) and methyl methacrylate (107 mL, 1 mol) are then added. The reaction mixture is refluxed for 2 hours, allowed to cool and the chloroform is then evaporated off. The residue is taken up in ethyl acetate and the organic phase is washed 3 times with water and once with saturated sodium chloride solution. A flash chromatography of the crude product (16.0 g) on silica gel (1 kg) with an elution gradient of from 30% to 70% ethyl acetate in petroleum ether gives the expected product in the form of white crystals (10.1 g, 40%). $^1$H NMR (300 MHz, δ ppm) DMSO D6: 1.15, (d, 3H), 3.05 (m, 1H), 3.50 (s, 3H), 4.25 (dd, 1H), 4.50 (dd, 1H), 7.25 (m, 2H), 7.60 (m, 2H).

1.3.2: Lithium 1-methyl-3-(2-chloro-1-benzimidazolyl)-propionate

This compound is obtained according to the method described in the preparation in point 1.2, by treating methyl 1-methyl-3-(2-chloro-1-benzimidazolyl)propionate with lithium hydroxide. $^1$H NMR (300 MHz, δ ppm) DMSO D6+εD$_2$O: 1.35 (d, 3H), 2.60 (m, 1H), 4.10 (dd, 1H), 4.40 (dd, 1H), 7.25 (m, 2H), 7.55 (d, 1H), 7.60 (d, 1H). LC-MS: MH$^+$=239 (acid).

1.3.3: 2-Chloro-5-methyl-4,5-dihydroimidazo[4,5,-ij]-quinolin-6-one

This compound is obtained from the lithium salt according to the method described in point 1.2 by treating it successively with oxalyl chloride to give the intermediate acid chloride, and with aluminium chloride. $^1$H NMR (300 MHz, δ ppm) DMSO D6: 1.40 (d, 3H), 3.20 (m, 1H), 4.10 (dd, 1H), 4.65 (dd, 1H), 7.45 (t, 1H), 7.70 (d, 1H), 7.85 (d, 1H). LC-MS: MH$^+$=221.

1.4 Preparation of 2-chloro-4,5-dihydro-9-methylimidazo[4,5,1-ij]quinolin-6-one (A=Cl, R1=9-CH$_3$, R2=R2'=H, n=1)

1.4.1. 2-Hydroxy-4-methylbenzimidazole 2,3-Diaminotoluene (5 g, 41 mmol), 1,1-carbonyldiimidazole (7.3 g, 45 mmol) and 50 mL of anhydrous DMF are successively introduced into a 250 mL two-necked flask under an argon atmosphere, with magnetic stirring. After heating the mixture at 90–95° C. for 4 h, the solvent is distilled off under vacuum and the residue obtained is taken up in water (250 mL) and extracted with ethyl acetate (3×250 mL). The insoluble product formed during the extraction is recovered (4.8 g) and the combined organic phases are washed again with saturated NaCl solution, dried over MgSO$_4$, filtered and concentrated to give a further 1.2 g of desired product (6 g, quantitative). $^1$H NMR (300 MHz, δ ppm) DMSO D6: 2.27 (s, 3H), 6.72 (m, 2H), 6.82 (m, 1H).

1.4.2. 2-Chloro-4-methylbenzimidazole

2-Hydroxy-4-methylbenzimidazole (5.92 g, 40 mmol) and 40 mL of phosphoryl chloride are introduced into a 250 mL two-necked flask under an argon atmosphere, with magnetic stirring. The mixture is refluxed for 20 hours and the phosphoryl chloride is evaporated off under vacuum. The solid obtained is taken up in water (250 mL), neutralized to pH=8 with 28% aqueous ammonia and the aqueous phase is extracted with ethyl acetate (3×250 mL). After the usual work-up, the title product is obtained in a yield of 93% (6.23 g). $^1$H NMR (300 MHz, δ ppm) DMSO D6: 2.47 (s, 3H), 7.01 (d, 1H), 7.11 (t, 1H), 7.32 (d, 1H).

1.4.3. Methyl 1-methyl-3-(2-chloro-4-methyl-1-benzimidazolyl)propionate

The title compound is prepared according to the procedure described in Example 1.3.1 (7.85 g, 94%). $^1$H NMR (300 MHz, δ ppm) DMSO D6: 2.48 (s, 3H), 2.86 (t, 2H), 3.56 (s, 3H), 4.49 (t, 2H), 7.06 (d, 1H), 7.19 (t, 1H), 7.44 (d, 1H).

1.4.4. Lithium 1-methyl-3-(2-chloro-4-methyl-1-benzimidazolyl)propionate

The title compound is prepared according to the procedure described in Example 1.3.2. (6.94 g, 94%). $^1$H NMR (300 MHz, δ ppm) DMSO D6: 2.3 (dd, 2H), 2.48 (s, 3H), 4.32 (dd, 2H), 7.01 (d, 1H), 7.15 (t, 1H), 7.41 (d, 1H) (acid).

1.4.5. 2-Chloro-4,5-dihydro-9-methylimidazo[4,5,1-ij]quinolin-6-one

The title compound is prepared according to the procedure described in Example 1.3.3. (4.72 g, 76%). $^1$H NMR (300 MHz, δ ppm) DMSO D6: 2.58 (s, 3H), 3.05 (t, 2H), 4.53 (t, 2H), 7.19, (d, 1H), 7.52 (d, 1H).

EXAMPLE 2

1-(6-Oxo-5,6-dihydro-4H-imidazo[4,5,1-ij]quinolin-2-yl)-4-piperidinopiperidine (R1=R2=R2'=R3=H, R4=1-piperidyl, X=C, n=m=1) (compound 45)

400 mg of chloro derivative of formula (II) described in point 1.1, 5 mL of dimethylformamide, 70 mg of potassium fluoride, 0.2 mL of 2,6-lutidine and 500 mg of 4-piperidinopiperidine are reacted together for 2 hours at 140° C. After evaporation of the solvent, the residue is chromatographed on silica gel (eluent: dichloromethane+8% methanol). 375 mg of product are obtained in the form of a whitish solid. $^1$H NMR (200 MHz, δ ppm) DMSO D6: 1.2–2.2 (m, 12H) 3.0 (M, 3H), 3.2–3.4 (m, 4H), 4.2 (d, 2H), 4.65 (t, 2H), 7.4 (t, 1H), 7.6, (d, 1H), 7.8 (d, 1H).

EXAMPLE 3

1-Methyl-1-[1-(6-oxo-5,6-dihydro-4H-imidazo[4,5,1-ij]quinolin-2-yl)-4-piperidinyl]piperidinium chloride (R1=R2=R2'=R3=H, R4=N-methyl-1-piperidyl, X=C, n=1, m=1) (compound 48)

3.1: 4-(N-piperidino) Boc Piperidine 3.98 g of 4-oxo-N-Boc piperidine, 1.7 g of piperidine and 7.1 g of Ti (IV) isopropoxide are mixed together in a three-necked round-bottomed flask under nitrogen, and the mixture is left stirring for one hour at room temperature. 20 mL of absolute ethanol and 850 mg of NaBH$_3$CN are then added. The resulting mixture is left to react for 17 hours at room temperature, 5 mL of water are added and the mixture is stirred for 5 minutes and filtered through Whatman paper. The pink solution is evaporated, the residue is taken up in 100 mL of ethyl acetate and the solution is dried over magnesium sulphate and evaporated. The residue obtained is chromatographed on 100 g of silica and eluted with acetone. 2.2 g of oil, which crystallizes, are obtained, the NMR spectrum of which corresponds to the expected structure, and the product is used without further purification for the following step.

3.2: N-Boc-4-(N-methylpiperidinium)piperidine chloride

The compound obtained above (2.2 g) is stirred with 5 mL of CH$_3$I for 17 hours in the absence of light, and then evaporated. 3.10 g of white crystals are obtained, which are used without further purification in the following step.

3.3: 4-(N-methylpiperidinium)piperidine chloride

The crystals obtained above are suspended in 20 mL of dichloromethane to which are added 5 mL of a saturated solution of hydrogen chloride in ether. The gummy precipitate obtained is redissolved in 20 mL of methanol, evaporated to dryness and taken up in 5 mL of methanol. This solution is cooled to 0° C., 1.35 mL of sodium methoxide (at 30% in methanol) are added and the mixture is stirred for 15 minutes, filtered and evaporated with a vacuum pump. The amine obtained is used without further purification for the following coupling.

3.4: 1-Methyl-1-[1-(6-oxo-5,6-dihydro-4H-imidazo[4,5,1-ij]quinolin-2-yl)-4-piperidyl]piperidinium chloride 400 mg of 2-chloro-4,5-dihydro-6H-imidazo[4,5,1-ij]quinolin-6-one in 5 mL of dimethylformamide, 70 mg of potassium fluoride, 0.2 mL of 2,6-lutidine and 1.6 g of 4-(N-methylpiperidinium)piperidine chloride are added to a three-necked flask under argon and left stirring for 5 hours at 140° C. The mixture is evaporated on a vacuum pump and the residue obtained is chromatographed with 70 g of Silica H (Merck) (eluent: dichloromethane with 10% methanol and 0.5% triethylamine). 50 mg of pure product are obtained, the NMR spectrum of which corresponds to the desired structure.

EXAMPLE 4

2-[4-(4-Dimethylamino-phenyl)piperazin-1-yl]4,5-dihydroimidazo[4,5,1-ij]quinolin-6-one (R1=R2=R2'=H, R3=–, R4=para-dimethylaminophenyl, X=N, n=m=1) (compound 58)

4.1: 1-(tert-Butoxycarbonyl)-4-(4-dimethylamino-phenyl)piperazine

1-Bromo-4-N,N-dimethylaniline (0.85 g, 4.25 mmol), palladium acetate (0.039 g, 0.17 mmol), 2,2'-bis(diphenylphosphino)-1,1'-binaphthyl (BINAP) (0.17 g, 0.25 mmol) and tBuOK (0.67 g, 5.95 mmol) are successively introduced into a round-bottomed flask under a nitrogen atmosphere, fitted with a condenser, with magnetic stirring. The flask is purged 3 times with nitrogen, toluene (25 mL) and N-tert-butoxycarbonylpiperazine (0.95 g, 5.1 mmol) are introduced and the reaction mixture is refluxed for 20 hours. After cooling to room temperature, ethyl acetate is added and the organic phase is washed twice with water. After drying the organic phase over sodium sulphate, filtering and concentrating, a residue (1.38 g) is obtained, which is chromatographed on silica gel with a gradient of dichloromethane/ethyl acetate (9/1 to 1/1). The title compound is obtained in a yield of 50% (0.67 g). $^1$H NMR (300 MHz, δ ppm) CDCl3: 1.47 (s, 9H), 2.99 (m, 4H), 3.57 (m, 4H), 6.72 (d, 2H), 6.89 (d, 2H).

4.2: N-1-(4-Dimethylaminophenyl)piperazine

The product described in Example 1.1 (0.67 g, 2.2 mmol) is dissolved in trifluoroacetic acid (trifluoroacetic acid, 20 mL) and maintained under magnetic stirring for 2.5 hours at room temperature. After evaporation of the trifluoroacetic acid, the residue is taken up in saturated sodium carbonate solution and the aqueous phase is extracted twice with ethyl acetate. The combined organic phases are washed to neutrality with saturated sodium chloride solution, dried over sodium sulphate and concentrated. After chromatography of the residue on silica gel (95/5/0.1 dichloromethane/methanol/NH$_4$OH), the title product is obtained in a yield of 69% (0.31 g, Rf: 0.1).

4.3: 2-[4-(4-Dimethylaminophenyl)piperazin-1-yl]4,5-dihydroimidazo[4,5,1-ij]quinolin-6-one The chloro intermediate described in point 1.1 (0.2 g, 0.969 mmol), 1 mL of triethylene glycol monomethyl ether (TGME), lutidine (0.125 mL, 1.07 mmol), cesium fluoride (0.148 g, 0.969 mmol) and a solution of the derivative of Example 1.2 (0.219 g, 1.07 mmol) in TGME (1 mL) are successively introduced into a round-bottomed flask fitted with a condenser, with magnetic stirring. The reaction mixture is heated at 140° C. for 1.5 hours and allowed to cool, water is added and the mixture is extracted twice with ethyl acetate. The organic phases are washed twice with water, dried over sodium sulphate, filtered and concentrated. The residue (0.38 g) is chromatographed on silica gel (ethyl acetate) and the oil obtained (0.246 g) is taken up in a small amount of dichloromethane and crystallized by adding ether. The white solid, which corresponds to the expected compound (0.208 g, 57%) is filtered off. LC-MS: MH+=376. $^1$H NMR (360 MHz, δ ppm) DMSO D6: 2.79 (s, 6H), 3.0 (t, 2H), 3.14 (m, 4H), 3.55 (m, 4H), 4.47 (t, 2H), 6.71 (d, 2H), 6.91 (d, 2H), 7.15 (dd, 1H), 7.35 (d, 1H), 7.60 (d, 1H).

EXAMPLE 5

2-[4-(4-tert-Butoxycarbonylamino-phenyl)piperazin-1-yl]-4,5-dihydroimidazo[4,5,1-ij]quinolin-6-one (R1=R2=R2'=H, R3=–, X=N, R4=4-tert-butyloxycarbonylaminophenyl, n=m=1) (compound 57)

5.1: 1-[2-(Trimethylsilyl)ethylcarbonyl]-4-(4-nitrophenyl)piperazine

A solution of 1-(4-nitrophenyl)piperazine (10 g, 48.31 mmol) and 2-(trimethylsilyl)ethyl p-nitrophenyl carbonate (14.4 g, 50.73 mmol) in tetrahydrofuran (220 mL) is refluxed for 3 hours with magnetic stirring and then stirred for 20 hours at room temperature. The reaction mixture is concentrated, the residue is taken up in dichloromethane and the organic phase is washed 4 times with 1N sodium hydroxide and twice with water. The organic phase is then dried over sodium sulphate, filtered and concentrated; the oily residue obtained is used without further purification in the following step (12 g, yield: 71%). $^1$H NMR (300 MHz, δ ppm) CDCl3: 0.04 (s, 9H), 1.02 (m, 2H), 3.43 (m, 4H), 3.65 (m, 4H), 4.22 (m, 2H), 6.82 (d, 2H), 8.13 (d, 2H).

5.2: 1-[2-(Trimethylsilyl)ethylcarbonyl]-4-(4-aminophenyl)piperazine

A mixture of the nitro derivative described above (12 g, 34.2 mmol) and of 4 to 5 spatulas of Raney nickel in 300 mL of ethanol is maintained under a hydrogen atmosphere, at atmospheric pressure, for 18 hours, with vigorous magnetic stirring. After filtration and concentration, the residue obtained is used without further purification in the following step: the expected product, which is present at about 50% according to the NMR and LC-MS, is difficult to purify. $^1$H NMR (300 MHz, δ ppm) CDCl3: 0.04 (s, 9H), 1.03 (m, 2H), 2.96 (m, 4H), 3.59 (m, 4H), 4.18 (m, 2H), aromatic protons not assignable, due to the presence of impurities.

5.3: 1-[2-(Trimethylsilyl)ethylcarbonyl]-4-(4-tert-butoxycarbonylaminophenyl)piperazine The crude reaction mixture from the above step (evaluated as 31 mmol) and di-tert-butyl dicarbonate (7.5 g, 34.1 mmol) in tetrahydrofuran (50 mL) are successively added to a round-bottomed flask fitted with a condenser, and the mixture is refluxed for 44 hours. The tetrahydrofuran is evaporated off, the residue is taken up in a water/ethyl acetate mixture and the organic phase is washed twice with water. The organic phase is dried over sodium sulphate and concentrated, and the residue is chromatographed on silica gel (1/1 dichloro-methane/ethyl acetate). The impure product obtained is used without further purification for the following step. LC-MS: MH+=422.

5.4: 1-(4-tert-Butoxycarbonylaminophenyl)piperazine

The intermediate described in the above point (3 g, considered as 7.12 mmol) and tetrabutylammonium fluoride (3.37 g, 10.68 mmol) in tetrahydrofuran (60 mL) are successively introduced into a round-bottomed flask equipped with a condenser, with magnetic stirring. The reaction mixture is refluxed for 2 hours and concentrated, and the residue is taken up in water and ethyl acetate. The organic phase is washed twice with water and then with saturated sodium chloride solution, dried over sodium sulphate and concentrated. The title compound (0.99 g, 50% over 3 steps) is obtained after chromatography on silica gel (90/10/0.1 dichloromethane/methanol/NH$_4$OH). $^1$H NMR (300 MHz, δ ppm) CDCl3: 1.50 (s, 9H), 3.04 (m, 8H), 6.60 (s, 1H), 6.87 (d, 2H), 7.23 (d, 2H).

5.5: 2-[4-(4-tert-Butoxycarbonylaminophenyl)piperazin-1-yl]-4,5-dihydroimidazo[4,5,1-ij]quinolin-6-one The chloro intermediate described in point 1.1 (0.7 g, 3.39 mmol), TGME (7 mL), lutidine (0.43 mL, 3.73 mmol), cesium fluoride (0.514 g, 3.39 mmol) and 1-(4-tert-butoxycarbonylaminophenyl)piperazine (1.03 g, 3.73 mmol) are successively introduced into a round-bottomed flask fitted with a condenser, with magnetic stirring. The reaction mixture is heated at 140° C. for 2 hours and allowed to cool, water is added and the mixture is extracted twice with ethyl acetate. The organic phases are washed twice with water, dried over sodium sulphate, filtered and concentrated. Chromatography of the residue on silica gel (dichloromethane/ethyl acetate gradient: 75/25 to 1/1) gives the expected compound, which is then crystallized in a dichloromethane/ether mixture to give a white solid (1.1 g, 73%). LC-MS: MH+=448. $^1$H NMR (500 MHz, δ ppm) DMSO D6: 1.45 (s, 9H), 3.00 (t, 2H), 3.22 (m, 4H), 3.55 (m, 4H), 4.47 (t, 2H), 6.91 (d, 2H), 7.15 (dd, 1H), 7.33 (m, 2H), 7.35 (d, 1H), 7.61 (d, 1H).

EXAMPLE 6

2-[4-(4-Aminophenyl)piperazin-1-yl]4,5-dihydroimidazo[4,5,1-ij]quinolin-6-one Dihydrochloride (R1=R2=R2'=H, R3=–, R4=para-aminophenyl, X=N, n=m=1) (compound 50)

A solution of hydrogen chloride gas in ethanol is added to the compound of Example 5 (0.22 g, 0.497 mmol) and the reaction mixture is stirred at room temperature for 2 hours. The resulting mixture is concentrated and the expected compound is obtained, after trituration from ether, in the form of a white solid (0.155 g, 80%). $^1$H NMR (500 MHz, δ ppm) DMSO D6: 3.06 (t, 2H), 3.63 (m,4H), 3.84 (m, 4H), 4.65 (t, 2H), 7.10 (d, 2H), 7.26 (d, 2H), 7.36 (dd, 1H), 7.54 (d, 1H), 7.71 (d, 1H), 10.06 (broad peak, 2H).

EXAMPLE 7

2-[4-(4-Acetamidophenyl)piperazin-1-yl]4,5-dihydroimidazo[4,5,1-ij]quinolin-6-one (R1=R2=R2'=H, R3=–, R4=para-acetamidophenyl, X=N, n=m=1) (compound 60)

The compound of Example 6 (0.20 g, 0.48 mmol) and triethylamine (80 µL, 0.572 mmol) are added to a solution of acetic acid (27 µL, 0.468 mmol) and carbonyldiimidazole (0.152 g, 0.936 mmol) in DMF (4 mL). The reaction mixture is maintained under magnetic stirring at 70° C. for 20 hours. After evaporation of the DMF under vacuum, the residue is taken up in water and triturated, and the solid obtained is filtered off. Washing the solid with a minimum amount of dichloromethane and then with ether gives the expected compound (0.12 g, 64%). $^1$H NMR (500 MHz, δ ppm) DMSO D6: 1.99 (s, 3H), 3.00 (t, 2H), 3.25 (m, 4H), 3.55 (m, 4H), 4.48 (t, 2H), 6.94 (d, 2H), 7.15 (dd, 1H), 7.35 (d, 1H), 7.44 (d, 2H), 7.61 (d, 1H), 9.70 (s, 1H).

EXAMPLE 8

2-(4-n-Propylpiperazin-1-yl)-4,5-dihydroimidazo[4,5,1-ij]quinolin-6-one dihydrochloride (R1=R2=R2'=R4=H, X=N, R3=n-propyl, n=m=1) (compound 26)

The intermediate of formula (II) from point 1.1 (0.2 g, 0.969 mmol), 1 mL of triethylene glycol monomethyl ether (TGME), lutidine (0.37 mL, 3.30 mmol), cesium fluoride (0.148 g, 0.969 mmol) and a solution of N-propylpiperazine dihydrobromide (0.296 g, 1.18 mmol) in TGME (1 mL) are successively introduced into a round-bottomed flask equipped with a condenser, with magnetic stirring. The reaction mixture is heated at 140° C. for 2 hours 15 minutes and allowed to cool, saturated sodium carbonate solution and solid sodium chloride are added and the mixture is extracted twice with ethyl acetate. The organic phases are washed twice with saturated sodium chloride solution, dried over sodium sulphate, filtered and concentrated. The residue obtained is chromatographed on silica gel (95/5/0.5 dichloromethane/methanol/NH$_4$OH) and the dihydrochloride salt of the oil obtained (0.203 g) is synthesized by dissolving it in a small amount of dichloromethane and adding a saturated solution of hydrogen chloride gas in anhydrous ether. The white solid, which corresponds to the expected product (0.23 g), is filtered off. LC-MS: MH+= 299. $^1$H NMR (360 MHz, δ ppm) DMSO D6: 0.94 (t, 3H), 1.78 (m, 2H), 3.08 (m, 4H), 3.28 (m, 2H), 3.62 (3, 2H), 3.88 (m, 2H), 4.25 (m, 2H), 4.65 (t, 2H), 7.42 (t, 1H), 7.60 (d, 1H), 7.76 (d, 1H), 11.66 (s, 1H).

EXAMPLE 9

2-(4-tert-Butyloxy-carbonylpiperazin-1-yl)-4,5-dihydroimidazo[4,5,1-ij]quinolin-6-one (R1=R2= R2'=H, R3=—, X=N, R4=tert-butyloxycarbonyl, n=m=1) (compound 12)

The intermediate described in point 1.1 (0.25 g, 1.2 mmol), TGME (1.5 mL), lutidine (0.155 mL, 1.33 mmol), cesium fluoride (0.184 g, 1.21 mmol) and a solution of tert-butyl-1-piperazine carboxylate (0.237 g, 1.28 mmol) in TGME (1.5 mL) are successively introduced into a round-bottomed flask equipped with a condenser, with magnetic stirring. The reaction mixture is heated at 120° C. for 3 hours and allowed to cool, water is added and this mixture is extracted twice with ethyl acetate. The organic phases are washed twice with water, dried over sodium sulphate, filtered and concentrated. The residue obtained is chromatographed on silica gel (1/1 dichloromethane/ethyl acetate) to give the expected compound in the form of a white solid (0.315 g, 73%). LC-MS: MH+=357. $^1$H NMR (500 MHz, δ ppm) DMSO D6: 1.51 (s, 9H), 3.07 (t, 2H), 3.46 (m, 4H), 3.58 (m, 4H), 4.52 (t, 2H), 7.23 (t, 1H), 7.43 (d, 1H), 7.68 (d, 1H).

EXAMPLE 10

2-(Piperazin-1-yl)-4,5-dihydroimidazo[4,5,1-ij] quinolin-6-one dihydrochloride (R1=R2=R2'=R3= R4=H, X=N, n=m=1) (compound 13)

A saturated solution of hydrogen chloride gas in anhydrous ether is added to a compound of Example 9 (0.1 g, 0.28 mmol) predissolved in a minimum amount of methanol, and the mixture is maintained under magnetic stirring at room temperature overnight. This mixture is concentrated and the residue is crystallized in a methanol/dichloromethane mixture. The expected compound is obtained in the form of a white solid (0.07 g). LC-MS: MH+=257. $^1$H NMR (500 MHz, δ ppm) DMSO D6: 3.12 (t, 2H), 3.95 (m, 4H), 3.94 (m, 4H), 4.66 (t, 2H), 7.43 (t, 1H), 7.61 (d, 1H), 7.80 (d, 1H), 9.63 (s, 2H).

EXAMPLE 11

2-(4-Acetylpiperazin-1-yl)-4,5-dihydroimidazo[4,5, 1-ij]quinolin-6-one dihydrochloride (R1=R2=R2'= H, R3=—, R4=COCH$_3$, X=N, n=m=1) (compound 15)

The compound of Example 10 (0.085 g, 0.26 mmol) and triethylamine (75 μL, 0.52 mmol) are added to a solution of acetic acid (20 μL, 0.349 mmol), hydroxybenzotriazole (0.055 g, 0.349 mmol) and diisopropyl azodicarboxylate (55 μL, 0.349 mmol) in dichloromethane (5 mL). The reaction mixture is maintained under magnetic stirring at room temperature overnight and is diluted with ethyl acetate and 1N hydrochloric acid solution. The crude product is obtained by the usual acid-base extraction and aqueous washes, followed by drying the organic phases over sodium sulphate and evaporation. A chromatography on silica gel (95/5 dichloromethane/ethanol) gives the expected compound (0.04 g). LC-MS: MH+=299. $^1$H NMR (500 MHz, δ ppm) DMSO D6: 2.13 (s, 3H), 3.08 (t, 2H), 3.46 (m, 2H), 3.52 (m, 2H), 3.70 (m, 4H), 4.54 (t, 2H), 7.23 (t, 1H), 7.43 (d, 1H), 7.68 (d, 1H).

EXAMPLE 12

2-[4-(4-Pyridyl)piperazin-1-yl]-4,5-dihydroimidazo [4,5,1-ij]quinolin-6-one Dihydrochloride (R1=R2= R2'=H, R3=—, R4=4-pyridyl, X=N, n=m=1) (compound 23)

The intermediate described in point 1.1 (0.2 g, 0.969 mmol), TGME (1 mL), lutidine (125 μL, 0.969 mmol), cesium fluoride (0.148 g, 0.969 mmol) and a solution of 1-(4-pyridyl)piperazine (0.238 g, 1.02 mmol) in TGME (1 mL) are successively introduced into a round-bottomed flask fitted with a condenser, with magnetic stirring. The reaction medium is heated at 140° C. for 1 hour 50 minutes and allowed to cool, saturated sodium carbonate solution and solid sodium chloride are added and the mixture is extracted twice with ethyl acetate. The organic phases are washed twice with saturated sodium chloride solution, dried over sodium sulphate, filtered and concentrated. The residue obtained is chromatographed on silica gel (95/5/0.5 dichloromethane/methanol/NH$_4$OH) to give the expected compound in the form of a white solid (0.071 g). LC-MS: MH+=334. $^1$H NMR (360 MHz, δ ppm) DMSO D6: 3.01 (t, 2H), 3.58 (m, 8H), 4.51 (t, 2H), 6.91 (d, 2H), 7.18 (t, 2H), 7.37 (d, 1H), 7.63 (d, 1H), 8.20 (d, 2H).

EXAMPLE 13

2-(4-Benzylpiperidin-1-yl)-4,5-dihydroimidazo[4,5, 1-ij]quinolin-6-one dihydrochloride (R1=R2=R2'= R3=H, R4=benzyl, X=C, n=m=1) (compound 1)

The intermediate described in point 1.1 (0.206 g, 1 mmol) dissolved in anhydrous toluene (8 mL), potassium tert-butoxide (0.157 mg, 1.4 mmol), 2,2'-bis (diphenylphosphino)-1,1'-binaphthyl (0.04 g, 0.06 mmol), palladium(II) acetate (0.009 g, 0.04 mmol) and a solution of, N-benzylpiperazine (0.21 g, 1.2 mmol) in toluene (2 mL) are successively introduced into a round-bottomed flask fitted with a condenser, with magnetic stirring and under a nitrogen atmosphere. The reaction mixture is heated at 85° C. overnight, allowed to cool, diluted with ethyl acetate and washed successively with water (3 times) and with saturated sodium chloride solution, dried over sodium sulphate, filtered and concentrated. The residue is chromatographed (0.24 g, 8/2 dichloromethane/ethyl acetate) to give the expected product (0.075 g). LC-MS: MH+=346. $^1$H NMR (360 MHz, δ ppm) DMSO D6: 1.37 (m, 1H), 1.67 (broad d, 1H), 1.80 (m, 1H), 2.58 (d, 1H), 2.84–3.00 (t, 2H and m, 1H), 3.81 (broad d, 1H), 4.40 (t, 2H), 7.12 (t, 1H), 7.20 (m, 3H), 7.26–7.37 (m, 1H and d, 1H), 7.5 (d, 1H)

EXAMPLE 14

1-(6-Oxo-5,6-dihydro-4H-imidazo[4,5,1-ij]quinolin-2-yl)-4-phenyl-4-piperidinecarboxamide (R1=R2=R2'=H, R3=CONH$_2$, R4=phenyl, X=C, n=m=1) (compound 43)

14.1: Compound of formula (III): 4-phenyl-piperidine-4-carboxamide

The compound is obtained according to the synthesis described in the literature: *Bioorg. Med. Chem. Lett.* 7(19), 1997, 2531–2536.

14.2: 1-(6-oxo-5,6-dihydro-4H-imidazo[4,5,1-ij] quinolin-2-yl)-4-phenyl-4-piperidinecarboxamide 300 mg of compound (II) described in point 1.1, 5 mL of dimethylformamide, 70 mg of potassium fluoride, 0.2 mL of 2,6-lutidine and 510 mg of compound (IV) described above are introduced into a 50 mL three-necked flask under nitrogen. The mixture is stirred for 4 hours at 140° C. and then evaporated under high vacuum. The residue obtained is chromatographed on silica gel (70–200 microns) with a mixture of 2% methanol in dichloromethane. The product obtained is then recrystallized from a minimum amount of hot acetone. 270 mg of white crystals are obtained. The signals in the NMR spectrum correspond to the expected product: $^1$H NMR (200 MHz, δ ppm) DMSO D6: 2.0 (m, 2H), 2.5 (m, 2H), 3.0 (t, 2H), 3.2–3.8 (m, 4H), 4.45 (t, 2H), 7.0–7.5 (m, 10H)

EXAMPLE 15

1-(6-Oxo-5,6-dihydro-4H-imidazo[4,5,1-ij]quinolin-2-yl)-4-phenyl-4-aminopiperidine Dihydrochloride (R1=R2=R2'=H, R3=NH$_2$, R4=phenyl, X=C, n=m=1) (compound 46)

4 mL of concentrated aqueous hydrochloric acid solution are added to compound 42 from the table (0.53 g, 1.21 mmol), manufactured according to the methods described above, predissolved in 5 mL of methanol and maintained under magnetic stirring at room temperature for 30 minutes. The mixture is concentrated under vacuum and the residue is taken up in absolute ethanol and then re-evaporated to dryness. The expected compound is obtained in the form of a white solid (0.45 g). $^1$H NMR (200 MHz, δ ppm) DMSO D6: 2.4–2.8 (m, 4H), 3.1 (t, 2H), 3.7 (m, 2H), 4.2 (m, 2H), 4.8 (t, 2H), 7.4–7.8 (m, 8H), 9.0 (s, 2H).

EXAMPLE 16

2-[4-(4-Hydroxyphenyl)-piperazin-1-yl]-4,5-dihydroimidazo[4,5,1-ij]quinolin-6-one (R1=R2=R2'=H, R3=–, X=N, R4=4-hydroxyphenyl, n=m=1) (compound 71)

16.1. 2-Chloro-4,5-dihydroimidazo[4,5,1-ij]quinolin-6-one ethylene ketal

A solution of the intermediate described in point 1.1 (0.6 g, 2.9 mmol) in 1,2-dichloroethane (10 mL), ethylene glycol (0.216 g, 3.49 mmol), p-toluenesulphonic acid (0.01 g) and trimethyl orthoformate (0.372 g, 3.49 mmol) are successively introduced into a round-bottomed flask fitted with a condenser, with magnetic stirring, and the mixture is completed with 13 mL of 1,2-dichloroethane. The resulting mixture is refluxed for 24 hours, the same amounts of the reagents (ethylene glycol, p-toluenesulphonic acid and trimethyl orthoformate) are added and the mixture is heated for a further 18 hours. After evaporation of the solvent, the residue is taken up in ethyl acetate and washed with dilute sodium carbonate solution and then with water, and the organic phase is dried and evaporated to dryness. The residue is chromatographed on silica gel (gradient: pure dichloromethane to 96/4 dichloromethane/ethyl acetate) to give the title compound (0.54 g, 74%). MH+=251.

16.2. Preparation of 2-[4-(4-benzyloxy-phenyl)piperazin-1-yl]-4,5-dihydroimidazo[4,5,1-ij]quinolin-6-one ethylene ketal The intermediate described in point 16.1 (0.54 g, 2.16 mmol), TGME (3 mL), lutidine (277 µL, 2.38 mmol), cesium fluoride (0.328 g, 2.16 mmol) and 1-(4-benzyloxyphenyl)piperazine (0.725 g, 2.38 mmol) are successively introduced into a round-bottomed flask fitted with a condenser, with magnetic stirring. The reaction medium is heated at 100° C. for 3 hours, lutidine is added (300 µL, 2.57 mmol) and the mixture is heated at 120° C. for 8 hours. The mixture is cooled, water is added and the resulting mixture is extracted twice with ethyl acetate. The organic phases are washed twice with water, dried over sodium sulphate, filtered and concentrated. The residue obtained is purified by chromatography twice on silica gel (gradient from 90/10 dichloromethane/ethyl acetate to 40/60 dichloromethane/ethyl acetate, and then gradient from ethyl acetate to 95/5 ethyl acetate/methanol) to give the expected compound contaminated with about 50% ketone originating from the hydrolysis of the ketal function (0.365 g). LC-MS: MH+= 483, MH+=439.

16.3. Preparation of 2-[4-(4-hydroxyphenyl)-piperazin-1-yl]-4,5-dihydroimidazo[4,5,1-ij]quinolin-6-one ethylene ketal The mixture of compounds from Example 16.2 (0.365 g), ethanol (60 mL), dichloromethane (about 0.5 mL) and 10% palladium-on-charcoal (0.04 g) are introduced into a round-bottomed flask and maintained under magnetic stirring and under a hydrogen atmosphere for 17 hours at room temperature. After filtration and evaporation of the solvent, the residue is chromatographed on silica gel (gradient from dichloromethane to 94/6 dichloromethane/methanol) to give the title product (0.132 g). $^1$H NMR (300 MHz, δ ppm) DMSO D6:2.2 (t, 2H), 3.13 (m, 4H), 3.46 (m, 3H), 4.08–4.20 (m, 4H), 4.21 (t, 2H), 6.68 (dd, 2H), 6.86 (dd, 2H), 7.04 (m, 2H), 7.32 (m, 1H), 8.91 (s, 1H).

16.4. Preparation of 2-[4-(4-hydroxyphenyl)-piperazin-1-yl]-4,5-dihydroimidazo[4,5,1-ij]quinolin-6-one 2-[4-(4-Hydroxyphenyl)piperazin-1-yl]-4,5-dihydroimidazo[4,5,1-ij]quinolin-6-one (0.055 g, 0.14 mmol) is dissolved in 11 mL of tetrahydrofuran and 3.6 mL of aqueous 5- hydrochloric acid solution are added. The mixture is left under magnetic stirring for 16 hours at room temperature and then at 50° C. for 2 hours. After dilution with water, the mixture is basified with sodium bicarbonate, extracted twice with ethyl acetate and the organic phases are dried over sodium sulphate. After the usual work-up, the residue is purified by chromatography on silica gel (gradient from dichloromethane to 94/6 dichloromethane/methanol)

to give the title product (0.027 g, 55%). $^1$H NMR (500 MHz, δ ppm) DMSO D6: 2.99 (t, 2H), 3.13 (m,4H), 3.53 (m, 4H), 4.47 (t, 2H), 6.67 (d, 2H), 6.85 (d, 2H), 7.15 (t, 1H), 7.34 (d, 1H), 7.60 (d, 1H), 8.88 (s, 1H).

EXAMPLE 17

2-[4-(4-Fluorophenyl)piperazin-1-yl]-4,5-dihydro-9-methylimidazo[4,5,1-ij]quinolin-6-one (R1=9-CH$_3$, R2=R2'=H, R3=–, X=N, R4=4-fluorophenyl, n=m=1) (compound 84)

The intermediate described in point 1.4 (0.2 g, 0.907 mmol), TGME (2 mL), lutidine (0.116 mL, 0.998 mmol), cesium fluoride (0.138 g, 0.907 mmol) and 4-fluorophenylpiperazine (0.180 g, 0.998 mmol) are successively introduced into a round-bottomed flask fitted with a condenser, with magnetic stirring. The reaction mixture is heated at 140° C. for 3 hours and allowed to cool, water is added and the mixture is extracted twice with ethyl acetate. The organic phases are washed twice with water, dried over sodium sulphate, filtered and concentrated. The residue obtained is chromatographed on silica gel (gradient from pure dichloromethane to 98/2 dichloro-methane/methanol) to give the expected compound in the form of a white solid (0.206 g, 62%). $^1$H NMR (500 MHz, δ ppm) DMSO D6: 2.50 (s, 3H), 2.97 (t, 2H), 3.28 (m, 4H), 3.54 (m, 4H), 4.45 (t, 2H), 7.05 (m, 5H), 7.29 (d, 1H).

EXAMPLE 18

1-[4-(4-Fluorophenyl)-piperazin-1-yl]-3-methyl-8,9-dihydro-7H-2,9a-diazabenzo[cd]azulen-6-one (R1=3-CH$_3$, R2=R2'=H, R3=–, X=N, R4=4-fluorophenyl, n=2, m=1) (compound 85)

1-Chloro-3-methyl-8,9-dihydro-7H-2,9a-diazabenzo[cd]azulen-6-one (0.2 g, 0.852 mmol), TGME (2 mL), lutidine (0.109 mL, 0.937 mmol), cesium fluoride (0.130 g, 0.852 mmol) and 4-fluorophenyl-piperazine (0.169 g, 0.937 mmol) are successively introduced into a round-bottomed flask fitted with a condenser with magnetic stirring. The reaction mixture is heated at 140° C. for 3.5 hours and allowed to cool, water is added and the mixture is extracted twice with ethyl acetate. After the usual work-up, the residue obtained is chromatographed on silica gel (gradient from pure dichloromethane to 60/40 dichloromethane/ethyl acetate) to give the title compound in the form of a white solid (0.137 g, 42%). $^1$H NMR (500 MHz, δ ppm) DMSO D6: 2.20 (m, 2H), 2.53 (s, 3H), 3.04 (m, 2H), 3.30 (m, 4H), 3.40 (m, 4H), 4.25 (m, 2H), 7.07 (m, 5H), 7.61 (d, 1H).

EXAMPLE 19

2-[4-(4-Fluorophenyl)piperazin-1-yl]-4,5-dihydro-7-methylimidazo[4,5,1-ij]quinolin-6-one (R1=7-CH$_3$, R2=R2'=H, R3=–, X=N, R4=4-fluoro-phenyl, n=m=1) (compound 83)

2-Chloro-4,5-dihydro-7-methylimidazo[4,5,1-ij]quinolin-6-one (0.245 g, 1.1 mmol), TGME (2.5 mL), lutidine (0.161 mL, 1.21 mmol), cesium fluoride (0.167 g, 1.1 mmol) and 4-fluorophenylpiperazine (0.219 g, 1.1 mmol) are successively introduced into a round-bottomed flask fitted with a condenser, with magnetic stirring. The reaction mixture is heated at 140° C. for 2.5 hours and allowed to cool, water is added and the mixture is extracted twice with ethyl acetate. After the usual work-up, the residue obtained is chromatographed on silica gel (gradient from 80/20 dichloromethane/ethyl acetate to 40/60 dichloromethane/ethyl acetate) to give the title compound in the form of a white solid (0.26 g, 65%). $^1$H NMR (500 MHz, δ ppm) DMSO D6: 2.59 (s, 3H), 2.98 (t, 2H), 3.26 (m, 4H), 3.49 (m, 4H), 4.42 (t, 2H), 6.94 (d, 1H), 7.05 (m, 4H), 7.50 (d, 1H).

EXAMPLE 20

2-[4-(4-Fluorophenyl)piperazin-1-yl]-4,5-dihydro-8-methylimidazo[4,5,1-ij]quinolin-6-one (R1=8—CH$_3$, R2=R2'=H, R3=–, X=N, R4=4-fluoro-phenyl, n=m=1) (compound 82)

The title compound is obtained from a ½ mixture of 2-chloro-4,5-dihydro-8-methylimidazo[4,5,1-ij]quinolin-6-one and 2-chloro-4,5-dihydro-7-methylimidazo[4,5,1-ij]quinolin-6-one, using the conditions described in Example 19. After chromatography on silica gel, two successive crystallizations gave the desired isomer contaminated with only 4% of the other isomer (0.053 g, yield calculated on the good isomer: 48%). $^1$H NMR (500 MHz, δ ppm) DMSO D6: 2.40 (s, 3H), 2.98 (t, 2H), 3.26 (m, 4H), 3.55 (m, 4H), 4.45 (t, 2H), 7.06 (m, 4H), 7.18 (s, 1H), 7.44 (s, 1 H).

EXAMPLE 21

2-[4-(4-Fluorophenyl)piperazin-1-yl]-4,5-dihydro-7-methoxyimidazo[4,5,1-ij]quinolin-6-one (R1=7—OCH$_3$, R2=R2'=H, R3=–, X=N, R4=4-fluorophenyl, n=m=1) (compound 81)

The title compound is obtained from 2-chloropiperazin-1-yl-4,5-dihydro-7-methoxyimidazo[4,5,1-ij]quinolin-6-one using the conditions described in Example 19 (29%). $^1$H NMR (500 MHz, δ ppm) DMSO D6: 2.89 (t, 2H), 3.26 (m, 4H), 3.44 (m, 4H), 3.81 (s, 3H), 4.36 (t, 2H), 6.79 (d, 1H), 7.06 (m, 4H), 7.58 (d, 1H).

The table which follows illustrates the chemical structures and the physical properties of a number of compounds of the invention corresponding to the general formula (I). Depending on whether n=1 or 2 in this formula, two compounds of formula (I) have been represented below with, for each of them, the numbering of the atoms on the benzimidazole nucleus.

In this table:

HCl represents a hydrochloride and CF$_3$CO$_2$H represents a trifluoroacetate salt, while "–" represents a compound in free form, Me, Et, n-Pr and tBu represent, respectively, methyl, ethyl, n-propyl and tert-butyl groups, Bn and Ph represent, respectively, benzyl and phenyl groups, except where otherwise mentioned, the NMR analyzes correspond to proton NMRs and the measurements are carried out in d$_6$-DMSO. * and ** mean that the measurements are carried out, respectively, at 360 MHz and at 500 MHz. If no indication of this type is given, then the measurement is carried out at 200 MHz.

TABLE

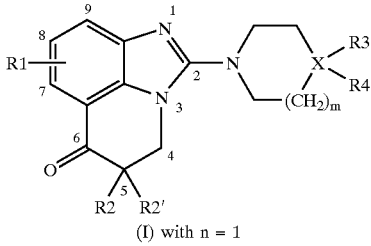

(I) with n = 1

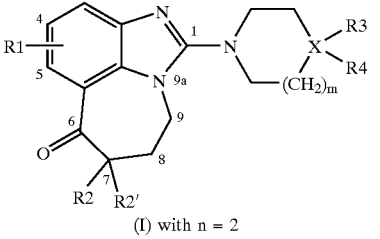

(I) with n = 2

| No. | R1 | R2 | R2' | R3 | R4 | X | n | M | Salt | NMR |
|---|---|---|---|---|---|---|---|---|---|---|
| 1 | H | H | H | H | Bn | C | 1 | 1 | — | 1.37 (m, 1H), 1.67 (broad d, 1H), 1.80 (m, 1H), 2.58 (d, 1H), 2.84–3.00 (t, 2H and m, 1H), 3.81 (broad d, 1H), 4.40 (t, 2H), 7.12 (t, 1H), 7.20 (m, 3H), 7.26–7.37 (m, 1H and d, 1H), 7.5 (d, 1H)* |
| 2 | H | H | H | — | Ph | N | 1 | 1 | — | 3.0 (t, 2H), 3.35 (m, 4H), 3.58 (m, 4H), 4.5 (t, 2H), 6.82 (t, 1H), 7.0 (d, 2H), 7.15 (t, 1H), 7.25 (t, 2H), 7.38 (d, 1H), 7.62 (d, 1H)* |
| 3 | H | H | H | — | 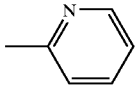 | N | 1 | 1 | — | 3.03 (t, 2H), 3.55 (m, 4H), 3.70 (m, 4H), 4.51 (t, 2H), 6.69 (t, 1H), 6.90 (d, 1H), 7.16 (t, 1H), 7.37 (d, 1H), 7.60 (m, 2H), 8.15 (d, 1H)* |
| 4 | H | H | H | — | 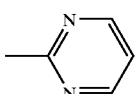 | N | 1 | 1 | — | 3.02 (t, 2H), 3.50 (m, 4H), 3.95 (m, 4H), 4.50 (t, 2H), 6.69 (t, 1H), 7.15 (t, 1H), 7.35 (d, 1H), 7.62 (d, 1H), 8.41 (d, 2H)* |
| 5 | H | H | H | — | 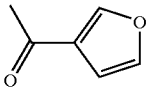 | N | 1 | 1 | — | 3.01 (t, 2H), 3.52 (m, 4H), 3.88 (m, 4H), 4.49 (t, 2H), 6.67 (s, 1H), 7.06 (d, 1H), 7.18 (t, 1H), 7.34 (d, 1H), 7.63 (d, 1H), 7.89 (s, 1H)* |
| 6 | H | H | H | — | 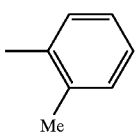 | N | 1 | 1 | — | 2.31 (s, 3H), 3.03 (m, 4H), 3.59 (m, 4H), 4.49 (t, 2H), 6.99 (t, 1H), 7.07 (d, 1H), 7.18 (m, 3H), 7.36 (d, 1H), 7.52 (d, 1H)* |
| 7 | H | H | H | — | 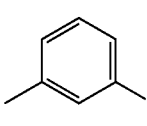 | N | 1 | 1 | — | 3.01 (t, 2H), 3.48 (m, 4H), 3.58 (m, 4H), 4.49 (t, 2H), 6.81 (d, 1H), 6.98 (d, 1H), 7.03 (s, 1H), 7.16 (t, 1H), 7.26 (t, 1H), 7.35 (d, 1H), 7.62 (d, 1H)* |
| 8 | H | H | H | — | 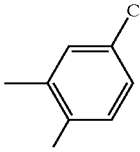 | N | 1 | 1 | — | 2.35 (s, 3H), 3.08 (t, 2H), 3.11 (m, 4H), 3.65 (m, 4H), 4.56 (t, 2H), 7.13 (m, 2H), 7.24 (t, 1H), 7.29 (d, 1H), 7.43 (d, 1H), 7.68 (d, 1H)** |
| 9 | H | H | H | — | 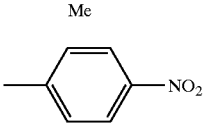 | N | 1 | 1 | — | 3.09 (t, 2H), 3.68 (m, 4H), 3.75 (m, 4H), 4.58 (t, 2H), 7.17 (d, 2H), 7.24 (t, 1H), 7.44 (d, 1H), 7.69 (d, 1H), 8.17 (d, 2H)** |
| 10 | H | H | H | — |  | N | 1 | 1 | — | 3.08 (t, 2H), 3.39 (m, 4H), 3.64 (m, 4H), 4.56 (t, 2H), 7.10 (d, 2H), 7.24 (t, 1H), 7.34 (d, 2H), 7.43 (d, 1H), 7.69 (d, 1H)** |
| 11 | H | H | H | — | Bn | N | 1 | 1 | — | 2.63 (m, 4H), 3.05 (t, 2H), 3.50 (m, 4H), 3.63 (s, 1H), 4.93 (t, 2H), 7.21 (t, 1H), 7.35 (m, 1H), 7.42 (m, 5H), 7.65 (d, 1H)** |

TABLE-continued

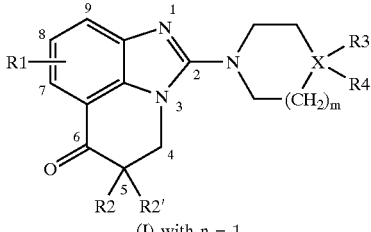
(I) with n = 1

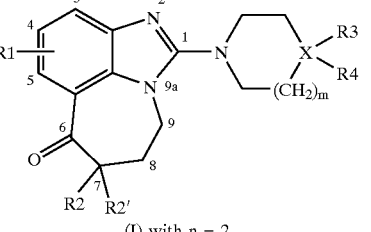
(I) with n = 2

| No. | R1 | R2 | R2' | R3 | R4 | X | n | M | Salt | NMR |
|---|---|---|---|---|---|---|---|---|---|---|
| 12 | H | H | H | — | 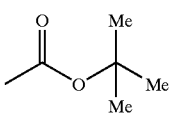 | N | 1 | 1 | — | 1.51 (s, 9H), 3.07 (t, 2H), 3.46 (m, 4H), 3.58 (m, 4H), 4.52 (t, 2H), 7.23 (t, 1H), 7.43 (d, 1H), 7.68 (d, 1H)** |
| 13 | H | H | H | H | H | N | 1 | 1 | 2HCl | 3.12 (t, 2H), 3.95 (m, 4H), 3.94 (m, 4H), 4.66 (t, 2H), 7.43 (t, 1H), 7.61 (d, 1H), 7.80 (d, 1H), 9.63 (s, 2H)** |
| 14 | H | H | H | — | 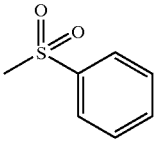 | N | 1 | 1 | — | 3.00 (t, 2H), 3.17 (m, 4H), 3.58 (m, 4H), 4.44 (t, 2H), 7.21 (t, 1H), 7.41 (d, 1H), 7.65 (d, 1H), 7.75 (m, 2H), 7.84 (m, 3H)** |
| 15 | H | H | H | — | —COMe | N | 1 | 1 | — | 2.13 (s, 3H), 3.08 (t, 2H), 3.46 (m, 2H), 3.52 (m, 2H), 3.70 (m, 4H), 4.54 (t, 2H), 7.23 (t, 1H), 7.43 (d, 1H), 7.68 (d, 1H)** |
| 16 | H | H | H | — | —CH₂COOEt | N | 1 | 1 | — | 1.2 (t, 3H), 2.7 (m, 2H), 2.97 (t, 2H), 3.32 (s, 2H), 3.41 (m, 2H), 4.43 (t, 2H), 7.12 (t, 1H), 7.32 (d, 1H), 7.59 (d, 1H)* |
| 17 | H | H | H | — |  | N | 1 | 1 | — | 3.1 (t, 2H), 3.29 (m, 4H), 3.58 (m, 4H), 4.50 (t, 2H), 7.05 (m, 4H), 7.17 (t, 1H), 7.35 (d, 1H), 7.62 (d, 1H)* |
| 18 | H | H | H | — | 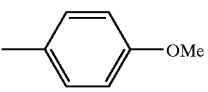 | N | 1 | 1 | — | 3.05 (t, 2H), 3.22 (m, 4H), 3.56 (m, 4H), 3.90 (s, 3H), 4.50 (t, 2H), 6.85 (d, 2H), 6.98 (d, 2H), 7.16 (t, 1H), 7.25 (d, 1H), 7.62 (d, 1H)* |
| 19 | H | H | H | — | 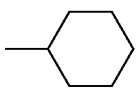 | N | 1 | 1 | — | 1.13 (m, 5H), 1.56 (m, 1H), 1.76 (m, 4H), 2.31 (m, 1H), 2.69 (m, 4H), 2.98 (t, 2H), 3.40 (m, 4H), 4.42 (t, 2H), 7.15 (t, 1H), 7.32 (d, 1H), 7.68 (d, 1H)* |
| 20 | H | H | H | — | 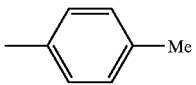 | N | 1 | 1 | — | 2.21 (s, 1H), 3.01 (t, 2H), 3.28 (m, 4H), 3.55 (m, 4H), 4.49 (t, 2H), 6.92 (d, 2H), 7.07 (d, 2H), 7.16 (t, 1H), 7.36 (d, 1H), 7.53 (d, 1H)* |
| 21 | H | H | H | — | 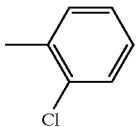 | N | 1 | 1 | — | 3.01 (t, 2H), 3.18 (m, 4H), 3.60 (m, 4H), 4.50 (t, 2H), 7.09 (t, 1H), 7.15 (t, 1H), 7.21 (d, 1H), 7.35 (m, 2H), 7.45 (d, 1H), 7.62 (d, 1H)* |
| 22 | H | H | H | — | 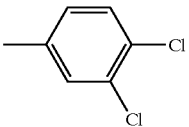 | N | 1 | 1 | — | 3.02 (t, 2H), 3.41 (m, 4H), 3.56 (m, 4H), 4.52 (t, 2H), 7.01 (d, 1H), 7.16 (t, 1H), 7.22 (s, 1H), 7.38 (d, 1H), 7.62 (d, 1H)* |
| 23 | H | H | H | — | 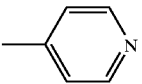 | N | 1 | 1 | — | 3.01 (t, 2H), 3.58 (m, 8H), 4.51 (t, 2H), 6.91 (d, 2H), 7.18 (t, 2H), 7.37 (d, 1H), 7.63 (d, 1H), 8.20 (d, 2H)* |

TABLE-continued (I) with n = 1

(I) with n = 2

| No. | R1 | R2 | R2' | R3 | R4 | X | n | M | Salt | NMR |
|---|---|---|---|---|---|---|---|---|---|---|
| 24 | H | H | H | H | Me | N | 1 | 1 | 2HCl | 2.84 (s, 3H), 3.08 (t, 2H), 3.27 (m, ≅2H), 3.55 (m, ≅2H) 3.72 (m, ≅2H), 4.14 (m, ≅2H), 4.59 (t, 2H), 7.35 (t, 1H), 7.52 (d, 1H), 7.75 (d, 1H), 11.42 (s, 1H)* |
| 25 | H | H | H | H | Et | N | 1 | 1 | 2HCl | Presence of 2 conformers, ~70/30: 1.32 (t, 3H), 2.31 (t, 0.6H), 3.08 (t, 1.4H), 3.19 (t, 2H), 3.60, 3.74, 3.89, 4.12, 4.24 (many multiplets, 8H), 4.35 (t, 0.6H), 4.55 (t, 1.4H), 7.36 (m, 1.4H), 7.50 (m, 0.9H), 7.73 (d, 0.7H), 11.28 (s, 0.7H), 11.55 (s, 0.3H)* |
| 26 | H | H | H | H | n-Pr | N | 1 | 1 | 2HCl | 0.94 (t, 3H), 1.78 (m, 2H), 3.08 (m, 4H), 3.28 (m, 2H), 3.62 (3, 2H), 3.88 (m, 2H), 4.25 (m, 2H), 4.65 (t, 2H), 7.42 (t, 1H), 7.60 (d, 1H), 7.76 (d, 1H), 11.66 (s, 1H)* |
| 27 | H | H | H | — | cyclohexyl | N | 2 | 1 | — | 1.30–1.60 (m, 6H), 1.70 (m, 2H), 1.85 (m, 2H), 2.20 (m, 2H), 2.40–2.60 (m, 3H), 2.90 (t, 2H), 3.05 (m, 2H), 3.65 (d, 2H), 4.20 (m, 2H), 7.20 (t, 1H), 7.65 (d, 1H), 7.70 (d, 1H)* |
| 28 | H | H | H | H | N-methylpiperidinyl | C | 2 | 1 | — | 1.10 (d, 1H), 1.20 (m, 4H), 1.60 (d, 1H), 1.80 (d, 4H), 2.20 (s, 2H), 2.30 (s, 1H), 2.70 (m, 4H), 3.05 (dd, 2H), 3.20 (s, 4H), 4.20 (s, 2H), 7.20 (t, 1H), 7.65 (d, 1H), 7.70 (d, 1H)* |
| 29 | H | H | H | H | Me | N | 1 | 2 | — | 1.96 (m, 2H), 2.29 (s, 3H), 2.56 (m, 2H), 2.74 (m, 2H), 2.99 (t, 2H), 3.73 (m, 4H), 4.49 (t, 2H), 7.08 (t, 1H), 7.22 (d, 1H), 7.43 (d, 1H)* |
| 30 | H | H | H | — | 4-methylphenyl-NHCHO | N | 1 | 1 | — | 3.01 (t, 2H), 3.29 (broad s, 4H), 3.58 (broad s, 4H), 4.49 (t, 2H), 6.98 (d, 2H), 7.16 (t, 1H), 7.35 (d, 1H), 7.48 (d, 2H), 7.61 (d, 1H), 8.2 (s, 1H), 9.98 (s, 1H)* |
| 31 | H | H | H | — | —COMe | N | 1 | 2 | — | Presence of 2 conformers, ~60/40: 1.86 (m, 0.8H), 1.54 (m, 1.2H), 2.03 (s, 3H), 3.04 (broad t, 2H), 3.55 (m, 2H), 3.78 (m, 2H), 3.89 (m, 2H), 7.31 (m, 1H), 7.45 (m, 1H), 7.6 (m, 1H)* |
| 32 | H | Me | H | — | Ph | N | 1 | 1 | — | 1.23 (s, 3H), 3.19 (m, 1H), 3.32 (m, 4H), 3.57 (m, 4H), 4.11 (t, 1H), 4.63 (dd, 1H), 6.81 (t, 1H), 7.01 (d, 2H), 7.17 (t, 1H), 7.26 (t, 2H), 7.37 (d, 1H), 7.61 (d, 1H)* |
| 33 | H | Me | H | — | 2-pyridyl | N | 1 | 1 | — | 1.22 (d, 3H), 3.18 (m, 1H), 3.52 (m, 4H), 3.68 (m, 4H), 4.12 (t, 1H), 4.62 (dd, 1H), 6.69 (dd, 1H), 6.9 (d, 1H), 7.17 (t, 1H), 7.36 (d, 1H), 7.57 (m, 1H), 7.6 (t, 1H) 8.14 (d, 1H)* |
| 34 | H | H | H | — | 3-pyridyl | N | 1 | 1 | — | 3.02 (t, 2H), 3.41 (m, 4H), 3.59 (m, 4H), 4.51 (t, 2H), 7.18 (t, 1H), 7.26 (m, 1H), 7.35 (d, 1H), 7.41 (m, 1H), 7.62 (d, 1H), 8.06 (d, 1H), 8.39 (s, 1H)* |

TABLE-continued (I) with n = 1 (left structure with positions 1,2,3,4,5,6,7,8,9 and R1, R2, R2', R3, R4, X, (CH2)m)

(I) with n = 2 (right structure with positions 1,2,3,4,5,6,7,8,9,9a and R1, R2, R2', R3, R4, X, (CH2)m)

| No. | R1 | R2 | R2' | R3 | R4 | X | n | M | Salt | NMR |
|---|---|---|---|---|---|---|---|---|---|---|
| 35 | H | H | H | — | Ph | N | 2 | 1 | — | 2.2 (m, 2H), 3.05 (m, 2H), 3.30 (m, 4H), 3.35 (m, 4H), 4.25 (m, 2H), 6.8 (t, 1H), 7.0 (d, 2H), 7.2 (t, 1H), 7.25 (d, 1H), 7.3 (d, 1H), 7.6 (d, 1H), 7.65 (d, 1H)* |
| 36 | H | H | H | H | H | C | 1 | 1 | — | 1.6 (s, 6H), 2.9 (t, 2H), 3.35 (m, 4H), 4.40 (t, 2H), 7.10 (t, 1H), 7.3 (d, 1H), 7.55 (d, 1H) |
| 37 | H | H | H | H | Ph | C | 1 | 1 | — | 1.95 (m, 4H), 2.85 (m, 1H), 3.20 (m, 4H), 4.0 (d, 2H), 4.5 (m, 2H), 7.2–7.4 (m, 7H), 7.65 (d, 1H) |
| 38 | H | H | H | —CO—NH$_2$ | H | C | 1 | 1 | — | 1.75 (m, 4H), 2.3 (m, 1H), 2.95 (m, 4H), 3.80 (d, 2H), 4.4 (t, 2H), 6.80 (s, 1H), 7.10 (t, 1H), 7.25 (d, 2H), 7.55 (d, 1H) |
| 39 | H | H | H | —OH | Ph | C | 1 | 1 | — | 1.6 (d, 2H), 2.05 (m, 2H), 2.90 (t, 2H), 3.2–3.8 (m, 4H), 4.4 (t, 2H), 5.05 (s, 1H), 7–7.6 (m, 8H) |
| 40 | H | H | H | NH—COMe | Ph | C | 1 | 1 | — | 1.8 (m, 2H), 1.85 (s, 3H), 2.4–2.6 (m, 2H), 3 (m, 2H), 3.6 (m, 2H), 3.90 (m, 2H), 4.70 (t, 2H), 7–7.6 (m, 8H) |
| 41 | H | H | H | —CH$_2$—OH | Ph | C | 1 | 1 | — | 2.1 (m, 2H), 2.3 (m, 2H), 3.0 (t, 2H), 3.3–3.5 (m, 4H), 3.95 (m, 2H), 4.60 (t, 2H), 7.2–7.8 (m, 8H) |
| 42 | H | H | H | —NH—COtBu | Ph | C | 1 | 1 | — | 1.1 (s, 9H), 2 (m, 2H), 2.5 (m, 2H), 2.90 (t, 2H), 3.2 (m, 2H), 3.70 (m, 2H), 4.4 (t, 2H), 7.1–7.4 (m, 8H), 7.55 (d, 1H) |
| 43 | H | H | H | CONH$_2$ | Ph | C | 1 | 1 | — | 2.0 (m, 2H), 2.5 (m, 2H), 3.0 (t, 2H), 3.2–3.8 (m, 4H), 4.45 (t, 2H), 7.0–7.5 (m, 10H) |
| 44 | H | H | H | —NH—CONH$_2$ | Ph | C | 1 | 1 | — | 2.0–2.6 (m, 4H), 3.1 (t, 2H), 3.4 (m, 2H), 3.8 (d, 2H), 4.5 (t, 2H), 5.5 (s, 2H), 6.6 (s, 1H), 7.2–7.6 (m, 7H), 7.7 (d, 1H) |
| 45 | H | H | H | H | N-methylpiperidine | C | 1 | 1 | — | 1.2–2.2 (m, 12H) 3.0 (m, 3H), 3.2–3.4 (m, 4H), 4.2 (d, 2H), 4.65 (t, 2H), 7.4 (t, 1H), 7.6, (d, 1H), 7.8 (d, 1H) |
| 46 | H | H | H | —NH$_2$ | Ph | C | 1 | 1 | 2HCl | 2.4–2.8 (m, 4H), 3.1 (t, 2H), 3.7 (m, 2H), 4.2 (m, 2H), 4.8 (t, 2H), 7.4–7.8 (m, 8H), 9.0 (s, 2H) |
| 47 | H | H | H | H | N-methylpyrrolidine | C | 1 | 1 | — | 1.5–2.0 (m, 8H), 3.0 (m, 4H), 3.2–3.6 (m, 5H), 4.1 (d, 2H), 4.6 (t, 2H), 7.3 (t, 1H), 7.5 (d, 1H), 7.6 (d, 1H) |
| 48 | H | H | H | H | N,N-dimethylpiperidinium | C | 1 | 1 | — | 1.5–2.0 (m, 10H), 2.1 (d, 2H), 2.8–3.0 (m, 4H), 3.1–3.6 (m, 3H), 4.1 (m, 2H), 4.6 (t, 2H), 7.4 (t, 1H), 7.6 (d, 1H), 7.7 (d, 1H) |
| 49 | H | Me | Me | — | Ph | N | 1 | 1 | — | 1.19 (s, 6H), 3.33 (m, 4H), 3.55 (m, 4H), 4.29 (s, 2H), 6.81 (t, 1H), 7.00 (d, 2H), 7.18 (t, 1H), 7.25 (t, 2H), 7.38 (d, 1H), 7.62 (d, 1H)** |

TABLE-continued (I) with n = 1 (left structure with positions 1-9, R1, R2, R2', R3, R4, X, (CH2)m)

(I) with n = 2 (right structure with positions 1-9a, R1, R2, R2', R3, R4, X, (CH2)m)

| No. | R1 | R2 | R2' | R3 | R4 | X | n | M | Salt | NMR |
|---|---|---|---|---|---|---|---|---|---|---|
| 50 | H | H | H | — | 4-aminophenyl-methyl | N | 1 | 1 | 2HCl | 3.06 (t, 2H), 3.63 (m, 4H), 3.84 (m, 4H), 4.65 (t, 2H), 7.10 (d, 2H), 7.26 (d, 2H), 7.36 (dd, 1H), 7.54 (d, 1H), 7.71 (d, 1H), 10.06 (broad peak, 2H)** |
| 51 | H | H | H | — | (4-fluorophenyl)carbonylmethyl | N | 1 | 1 | — | 3.0 (t, 2H), 3.71 (m, 8H), 4.47 (t, 2H), 7.16 (dd, 1H), 7.32 (dd, 2H), 7.36 (d, 1H), 7.55 (dd, 2H), 7.62 (d, 1H); $^{19}$F: 51.6 (m, 1F)* |
| 52 | H | H | H | — | (pyridin-4-yl)carbonylmethyl | N | 1 | 1 | — | 3.0 (t, 2H), 3.44 (m, 4H), 3.56 (m, 2H), 3.83 (m, 2H), 4.48 (t, 2H), 7.16 (dd, 1H), 7.36 (d, 1H), 7.47 (d, 2H)* |
| 53 | H | H | H | — | 2-oxoheptyl | N | 1 | 1 | — | 0.88 (t, 3H), 1.30 (m, 4H), 1.53 (m, 2H), 2.37 (t, 2H), 3.01 (t, 2H), 3.41 (m, 2H), 3.44 (m, 2H), 3.64 (m, 4H), 4.47 (t, 2H), 7.16 (dd, 1H), 7.35 (d, 1H), 7.61 (d, 1H)* |
| 54 | H | Me | H | H | 4,5-dimethylimidazolyl-methyl | C | 1 | 1 | — | Presence of 2 conformers. 1.21 (d, 3H), 1.74 m, 2H), 1.94 (m, 2H), 2.14 (m, 3H), 2.80 (m, 1H), 3.13 (m, 3H), 3.95 (m, 2H), 4.11 (t, 1H), 4.58 (m, 1H), 7.15 (dd, 1H), 7.35 (m, 2H), 7.59 (d, 1H), 11.57 (m, 1H)* |
| 55 | H | H | H | H | 4,5-dimethylimidazolyl-methyl | C | 2 | 1 | — | Presence of 2 conformers. 1.75 (m, 2H), 1.95 (m, 2H), 2.12 (2s 40/60, 3H), 2.23 (m, 2H), 2.79, (2m 40/60, 1H), 3.05 (m, 4H), 3.65 (m, 2H), 4.24 (m, 2H), 7.19 (dd, 1H), 7.36 (s, 1H), 7.68 (m, 2H), 11.54 (2s, 40/60, 1H)* |
| 56 | H | H | H | — | 2-phenylethyl | N | 1 | 1 | — | 2.58 (t, 2H), 2.62 (m, 4H), 2.78 (t, 2H), 2.98 (t, 2H), 3.42 (m, 4H), 4.43 (t, 2H), 7.14 (dd, 1H), 7.19 (m, 1H), 7.26 (m, 4H), 7.33 (d, 1H), 7.56 (d, 1H)** |
| 57 | H | H | H | — | 4-(tert-butoxycarbonylamino)phenyl-methyl | N | 1 | 1 | — | 1.45 (s, 9H), 3.00 (t, 2H), 3.22 (m, 4H), 3.55 (m, 4H), 4.47 (t, 2H), 6.91 (d, 2H), 7.15 (dd, 1H), 7.33 (m, 2H), 7.35 (d, 1H), 7.61 (d, 1H)** |
| 58 | H | H | H | — | 4-(dimethylamino)phenyl-methyl | N | 1 | 1 | — | 2.79 (s, 6H), 3.0 (t, 2H), 3.14 (m, 4H), 3.55 (m, 4H), 4.47 (t, 2H), 6.71 (d, 2h), 6.91 (d, 2H), 7.15 (dd, 1H), 7.35 (d, 1H), 7.60 (d, 1H)** |

TABLE-continued
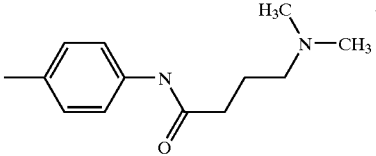
(I) with n = 1
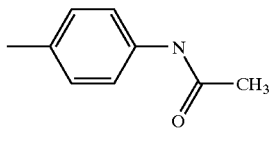
(I) with n = 2
| No. | R1 | R2 | R2' | R3 | R4 | X | n | M | Salt | NMR |
|---|---|---|---|---|---|---|---|---|---|---|
| 59 | H | H | H | — | 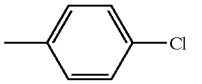 | N | 1 | 1 | — | 1.69 (tt, 1H), 2.13 (s, 6H), 2.22 (t, 2H), 2.22 (t, 2H), 3.00 (t, 2H), 3.27 (m, 4H), 3.55 (m, 4H), 4.48 (t, 2H), 6.94 (d, 2H), 7.15 (dd, 1H), 7.35 (d, 1H), 7.46 (d, 2H), 7.61 (d, 1H) 9.68 (s, 1H)** |
| 60 | H | H | H | — | 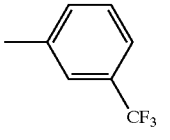 | N | 1 | 1 | — | 1.99 (s, 3H), 3.00 (t, 2H), 3.25 (m, 4H), 3.55 (m, 4H), 4.48 (t, 2H), 6.94 (d, 2H), 7.15 (dd, 1H), 7.35 (d, 1H), 7.44 (d, 2H), 7.61 (d, 1H), 9.70 (s, 1H)** |
| 61 | H | H | H | —OH | 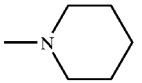 | C | 1 | 1 | — | 1.5–1.7 (d, 2H), 2.0–2.1 (d, 2H), 2.9 (t, 2H), 3.3–3.5 (t, 2H), 2.7–2.8 (d, 2H), 4.4 (t, 2H), 5.2 (s, 1H), 7.0–7.6 (m, 7H) |
| 62 | H | H | H | —OH | 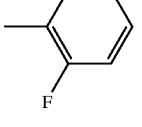 | C | 1 | 1 | — | 1.6–1.8 (m, 2H), 2.1–2.3 (m, 2H), 2.9 (t, 2H), 3.3–3.5 (t, 2H), 3.6–3.8 (d, 2H), 4.4 (t, 2H), 5.4 (s, 1H), 7.0–8.0 (m, 7H) |
| 63 | H | H | H | H | Ph | C | 1 | 2 | — | 1.6–2.2 (m, 6H), 2.6–4 (m, 8H), 4.8 (m, 1H), 7.1–7.3 (m, 5H), 7.4 (t, 1H), 7.6 (m, 2H) |
| 64 | H | H | H | —CO—NH$_2$ | 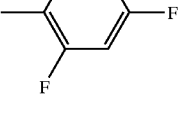 | C | 1 | 1 | 2 CF$_3$CO$_2$H | 1.2–2.4 (m, 8H), 2.6–3.7 (m, 10H), 4.2 (d, 2H), 4.7 (t, 2H), 7.4 (t, 1H), 7.6 (d, 1H), 7.8 (d, 1H), 8.2 (d, 2H) |
| 65 | H | H | H | — | 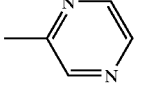 | N | 1 | 1 | — | 3.01 (t, 2h), 3.20 (m, 4H), 3.59 (m, 4H), 4.48 (t, 2H), 7.01 (m, 1H), 7.14 (m, 4H), 7.36 (d, 1H), 7.62 (d, 1H) |
| 66 | H | H | H | — | 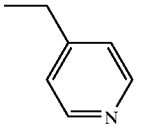 | N | 1 | 1 | — | 3.01 (t, 2H), 3.15 (m, 4H), 3.58 (m, 4H), 4.48 (t, 2H), 7.03 (m, 1H), 7.15 (m, 2H), 7.24 (m, 1H), 7.36 (d, 1H), 7.62 (d, 1H) |
| 67 | H | H | H | — |  | N | 1 | 1 | — | 3.01 (t, 2H), 3.54 (m, 4H), 3.76 (m, 4H), 4.49 (t, 2H), 7.15 (t, 1H), 7.35 (d, 1H), 7.61 (d, 1H), 7.88 (d, 1H), 8.12 (d, 1H), 8.39 (s, 1H) |
| 68 | H | H | H | — |  | N | 1 | 1 | — | 2.56 (m, 4H), 2.96 (t, 2H), 3.43 (m, 4H), 3.59 (s, 2H), 4.41 (t, 2H), 7.13 (t, 1H), 7.32 (d, 1H), 7.35 (d, 2H), 7.58 (d, 1H), 8.52 (d, 2H) |

TABLE-continued

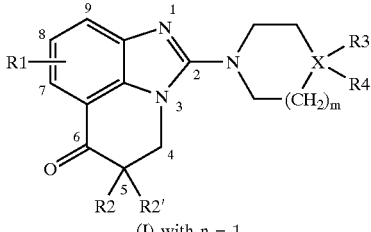

| No. | R1 | R2 | R2' | R3 | R4 | X | n | M | Salt | NMR |
|---|---|---|---|---|---|---|---|---|---|---|
| 69 | H | H | H | — | 2,6-dimethylpyridin-3-yl | N | 1 | 1 | — | 2.32 (s, 3H), 3.00 (t, 2H), 3.51 (m, 4H), 3.66 (m, 4H), 4.49 (t, 2H), 6.55 (d, 1H), 6.67 (d, 1H), 7.15 (t, 12H), 7.35 (d, 1H), 7.46 (t, 1H), 7.61 (d, 1H) |
| 70 | H | H | H | — | cycloheptyl | N | 1 | 1 | — | 1.43 (m, 2H), 1.50 (m, 6H), 1.61 (m, 2H), 1.74 (m, 2H), 2.49 (m, 1H), 2.62 (m, 4H), 2.97 (t, 2H), 3.37 (m, 4H), 4.41 (t, 2H), 7.12 (t, 1H), 7.32 (d, 1H), 7.57 (d, 1H) |
| 71 | H | H | H | — | 4-hydroxyphenyl | N | 1 | 1 | — | 2.99 (t, 2H), 3.13 (m, 4H), 3.53 (m, 4H), 4.47 (t, 2H), 6.67 (d, 2H), 6.85 (d, 2H), 7.15 (t, 1H), 7.34 (d, 1H), 7.60 (d, 1H), 8.88 (s, 1H) |
| 72 | H | H | H | — | 2-(thiophen-2-yl)ethyl | N | 1 | 1 | — | 2.62 (m, 6H), 2.99 (m, 4H), 3.422 (m, 4H), 4.43 (t, 2H), 6.92 (m, 2H), 7.14 (t, 1H), 7.32 (m, 2H), 7.58 (d, 1H) |
| 73 | H | H | H | — | 3-phenylpropyl | N | 1 | 2 | — | 2.34 (m, 2H), 3.12 (m, 4H), 3.67 (m, 8H), 4.20 (m, 2H), 4.67 (m, 2H), 7.30 (m, 6H), 7.53 (m, 1H), 7.68 (m, 1H), 11.37 (m, 1H) |
| 74 | H | H | H | — | 5-phenylpentyl | N | 1 | 1 | — | 1.47 (m, 2H), 1.60 (m, 2H), 2.36 (t, 2H), 2.50 (m, 4H), 2.60 (t, 2H), 2.98 (t, 2H), 3.39 (m, 4H), 4.42 (t, 2H), 7.14 (t, 1H), 7.16–7.30 (m, 5H), 7.33 (d, 1H), 7.58 (d, 1H) |
| 75 | H | H | H | — | 3-(pyridin-4-yl)propyl | N | 1 | 1 | — | 1.79 (m, 2H), 2.35 (m, 2H), 2.54 (m, 4H), 2.64 (t, 2H), 2.98 (t, 2H), 3.41 (m, 4H), 4.42 (t, 2H), 7.14 (t, 1H), 7.26 (d, 2H), 7.33 (d, 1H), 7.58 (d, 1H), 8.45 (d, 2H) |
| 76 | H | H | H | —NH₂ | H | C | 1 | 1 | HCl | 1.6–2.2 (m, 4H), 3.0 (t, 2H), 3.5 (m, 3H), 4.1 (d, 2H), 4.6 (t, 2H), 7.4 (t, 1H), 7.6 (d, 1H), 7.75 (d, 1H), 8.5 (s, 2H) |
| 77 | H | H | H | H | pyridin-4-ylmethyl | C | 1 | 1 | — | 1.92 (m, 4H), 2.9 (m, 1H), 3.0–3.2 (m, 5H), 4.0 (d, 2H), 4.45 (t, 2H), 7.2 (t, 1H), 7.3 (m, 4H), 7.6 (d, 1H), 8.5 (d, 2H) |
| 78 | H | H | H | — | (1-methylpiperidin-4-yl)methyl | N | 1 | 1 | — | 1.39 (m, 1H), 1.72 (m, 2H), 1.83 (m, 2H), 2.12 (s, 3H), 2.19 (m, 1H), 2.64 (m, 4H), 2.78 (m, 2H), 2.97 (t, 2H), 3.39 (m, 4H), 4.41 (t, 2H), 7.13 (t, 1H), 7.32 (d, 1H), 7.56 (d, 1H) |
| 79 | H | H | H | — | 4-(benzyloxy)phenylmethyl | N | 1 | 1 | — | 3.00 (t, 2H), 3,20 (m, 4H), 3.55 (m, 4H), 4.47 (t, 2H), 5.03 (s, 2H), 6.94 (m, 4H), 7.15 (t, 1H), 7.37 (m, 6H), 7.60 (d, 1H) |

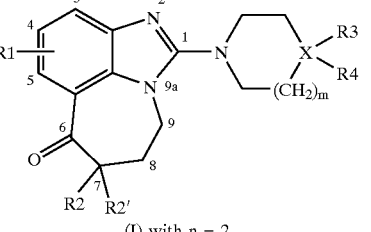
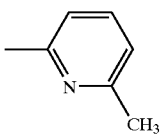
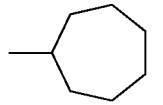
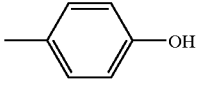
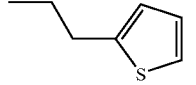
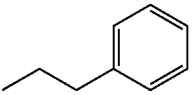
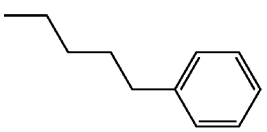
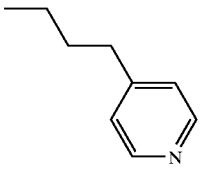
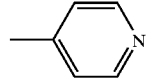
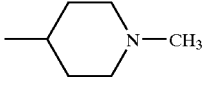
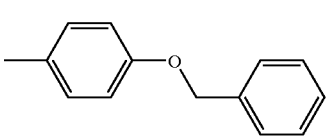

TABLE-continued

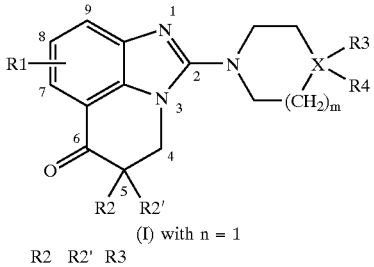

(I) with n = 1

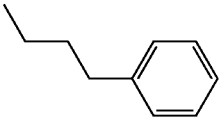

(I) with n = 2

| No. | R1 | R2 | R2' | R3 | R4 | X | n | M | Salt | NMR |
|---|---|---|---|---|---|---|---|---|---|---|
| 80 | H | H | H | — | 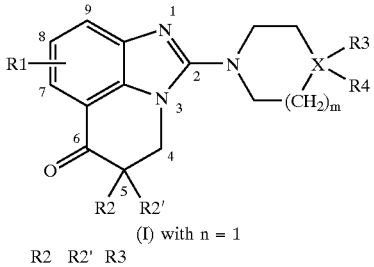 | N | 1 | 1 | — | 1.76 (m, 2H), 2.34 (t, 2H), 2.53 (m, 4H), 2.61 (t, 2H), 2.97 (t, 2H), 3.39 (m, 4H), 4.42 (t, 2H), 7.14 (m, 2H), 7.21 (m, 2H), 7.27 (m, 2H), 7.32 (d, 1H), 7.57 (d, 1H) |
| 81 | 7-OMe | H | H | — | 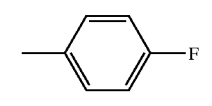 | N | 1 | 1 | — | 2.89 (t, 2H), 3.26 (m, 4H), 3.44 (m, 4H), 3.81 (s, 3H), 4.36 (t, 2H), 6.79 (d, 1H), 7.06 (m, 4H), 7.58 (d, 1H) |
| 82 | 8-Me | H | H | — | 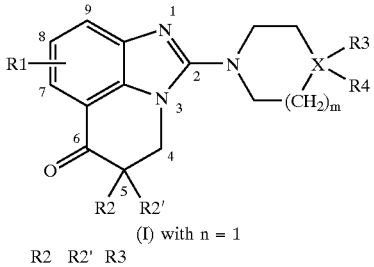 | N | 1 | 1 | — | 2.40 (s, 3H), 2.98 (t, 2H), 3.26 (m, 4H), 3.55 (m, 4H), 4.45 (t, 2H), 7.06 (m, 4H), 7.18 (s, 1H), 7.44 (s, 1H) |
| 83 | 7-Me | H | H | — | 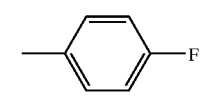 | N | 1 | 1 | — | 2.59 (s, 3H), 2.98 (t, 2H), 3.26 (m, 4H), 3.49 (m, 4H), 4.42 (t, 2H), 6.94 (d, 1H), 7.05 (m, 4H), 7.50 (d, 1H) |
| 84 | 9-Me | H | H | — | 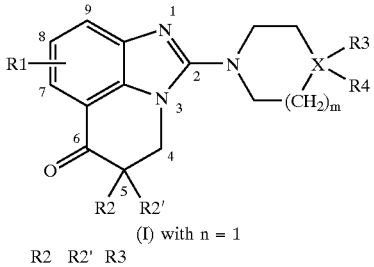 | N | 1 | 1 | — | 2.50 (s, 3H), 2.97 (t, 2H), 3.28 (m, 4H), 3.54 (m, 4H), 4.45 (t, 2H), 7.05 (m, 5H), 7.29 (d, 1H) |
| 85 | 3-Me | H | H | — | 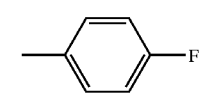 | N | 2 | 1 | — | 2.20 (m, 2H), 2.53 (s, 3H), 3.04 (m, 2H), 3.30 (m, 4H), 3.40 (m, 4H), 4.25 (m, 2H), 7.07 (m, 5H), 7.61 (d, 1H) |
| 86 | H | H | H | —N(—Me)$_3$$^+$ Cl$^-$ | H | C | 1 | 1 | — | 2.2 (m, 2H), 2.4 (m, 2H), 3.0 (m, 2H), 3.2 (s, 9H), 3.4 (m, 2H), 3.5 (m, 1H), 4.5 (m, 2H), 4.7 (m, 2H), 7.5 (t, 1H), 7.75 (d, 1H), 7.9 (d, 1H) |
| 87 | H | H | H | — | 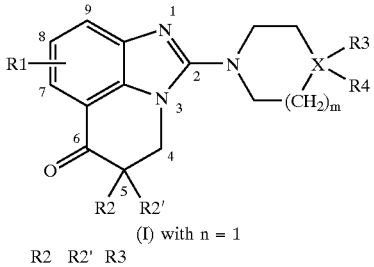 | N | 1 | 1 | — | 1.10 (m, 2H), 1.30 (s, 9H), 1.65 (m, 2H), 2.4 (m, 1H), 2.60 (m, 6H), 3.0 (t, 2H), 3.4 (m, 4H), 3.95 (m, 2H), 4.4 (t, 2H), 7.1 (t, 1H), 7.25 (d, 1H), 7.6 (d, 1H) |
| 88 | H | H | H | — | 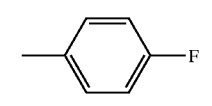 | N | 1 | 1 | — | 2.0 (m, 2H), 2.4 (m, 2H), 3.0–3.3 (m, 2H), 3.5 (m, 3H) 4.0 (m, 2H), 4.7 (m, 2H), 7.45 (t, 1H), 7.60 (d, 1H), 7.8 (d, 1H) |
| 89 | H | H | H | —NH—Me | H | C | 1 | 1 | 2 CF$_3$CO$_2$H | 1.8 (m, 2H), 2.30 (m, 2H), 2.75 (s, 3H), 3.2 (m, 2H), 3.5 (m, 1H), 3.45 (m, 2H), 4.2 (m, 2H), 4.75 (m, 2H), 7.5 (t, 1H), 7.65 (d, 1H), 7.8 (d, 1H) |
| 90 | H | H | H | —N—(Me)$_2$ | H | C | 1 | 1 | 2 CF$_3$CO$_2$H | 1.75 (m, 2H), 2.10 (m, 2H), 2.65 (s, 6H), 3.4 (m, 1H), 3.25 (m, 2H), 4.15 (m, 2H), 4.60 (t, 2H), 7.6 (t, 1H), 7.5 (d, 1H), 7.7 (d, 1H) |
| 91 | H | H | H | —OH | 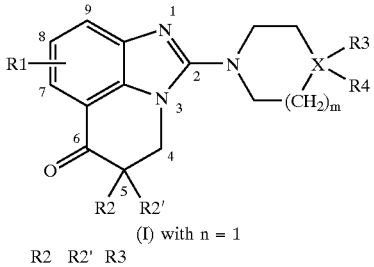 | C | 1 | 1 | — | 1.65 (d, 2H), 2.4 (m, 2H), 3.10 (t, 2H), 3.5 (m, 2H), 3.8 (m, 2H), 4.5 (t, 2H), 5.45 (s, 1H), 7.1–7.4 (m, 3H), 7.6–7.9 (m, 3H), 8.6 (d, 1H) |

The compounds of the invention underwent pharmacological tests to determine their inhibitory effect on PARP or poly(ADP-ribose)polymerase.

The compounds of the invention were subjected to the following test:

Effects of the Compounds on the Enzymatic Activity of PARP

Recombinant human PARP-1 (hPARP-1) is produced by the Sf9 cells using a baculovirus expression system (Giner et al., *Gene* (1992) 114 279–283). The enzyme is partially purified from the cell extract obtained after precipitation with 70% ammonium sulphate. The hPARP-1 solution obtained is capable of generating 0.5–0.7 nmol of nicotinamide from NAD+ under the standard test conditions described below. The test compounds are dissolved in an incubation medium containing 50 mM of Tris-HCl, 10 mM of $MgCl_2$, 20 µM of zinc acetate, 1.5 mM of dithiothreitol, 0.2 µg of histone and 0.1 µg of oligonucleotide (GGAATTCC) per 100 µL, in the presence of partially purified hPARP-1 buffered to pH8. The enzymatic reaction is initiated by addition of NAD+ (0.2 mM) and monitored at room temperature for 20 minutes. The reaction is stopped by the addition of $HClO_4$ (1.2 M) at 4° C. After centrifugation, the supernatants are analysed by HPLC (Shandon Ultrabase C8 column). Isocratic elution is performed using a phosphate buffer (0.1 M) of pH 4.5 containing 6% acetonitrile, injected at 1.25 mL/min for 6 minutes. The nicotinamide formed is detected by measuring the UV absorbence of the eluate at 265 nm and is quantified relative to the peak formed with an external standard of nicotinamide (2 nmol). The residual hPARP-1 activity measured in the presence of variable concentrations of compounds of the invention is compared with that obtained in their absence. All the measurements are carried out at least in duplicate, and the $IC_{50}$ values are calculated using the effect-dose sigmoid equation.

The compounds that are most active in this test are characterized by $IC_{50}$ values of between 5 and 500 nM.

Moreover, the compounds in accordance with the invention are also active towards PARP-2, the compounds that are most active towards this enzyme also being characterized by $IC_{50}$ values of between 5 and 500 nM.

It thus appears that the compounds of the invention have selective inhibitory activity on PARP, in particular PARP-1 and PARP-2.

The compounds of the invention may thus be used for the preparation of medicinal products, in particular PARP-inhibiting medicinal products. These medicinal products find their use in therapy, in particular in the prevention or treatment of myocardial infarction, cardiac ischemia, cardiac insufficiency, atherosclerosis, restenosis after PTCA or bypass, cerebral ischemia and cerebral infarction, caused by an ischemia, a trauma or a thromboembolic accident, neurodegenerative diseases such as Parkinson's disease, Alzheimer's disease and Huntington's chorea, acute renal insufficiency, in particular that of ischemic origin or appearing after kidney transplant, heart transplant: treatment of graft rejection and accelerated atherosclerosis of grafts, inflammatory pathologies, immunological disorders, rheumatoid diseases, diabetes and pancreatitis, septic shock, acute respiratory distress syndrome, tumours and metastases, autoimmune diseases, AIDS, hepatitis, psoriasis, vasculitis, ulcerative colitis, multiple sclerosis and myasthenia.

Thus, the compounds of formula (I) in accordance with the invention may be used for the preparation of a medicinal product for treating and preventing disorders in which the enzyme PARP is involved.

According to another aspect, a subject of the present invention is the use of the compounds of formula (I) for which R1=R2=R2'=R3=H, X=C, n=m=1 and R4 represents either a 4-imidazolyl group or a 5-methyl-4-imidazolyl group, for the manufacture of a medicinal product for treating or preventing disorders in which the enzyme poly (ADP-ribose) polymerase or PARP is involved, such as those mentioned above.

Finally, the present invention also relates to pharmaceutical compositions containing a compound according to the invention as active principle. These pharmaceutical compositions contain an effective dose of a compound according to the invention, and also one or more suitable pharmaceutical excipients. The said excipients are chosen according to the desired pharmaceutical form and mode of administration.

In the pharmaceutical compositions of the present invention for oral, sublingual, subcutaneous, intramuscular, intravenous, topical, intratracheal, intranasal, transdermal or rectal administration, the active principle of formula (I) above, or the possible salt or hydrate thereof, may be administered in a unit form of administration, mixed with conventional pharmaceutical excipients, to animals and to human beings for the prophylaxis or treatment of the above disorders or disease. The unit forms of administration that are appropriate comprise oral-route forms such as tablets, gel capsules, powders, granules and oral solutions or suspensions, sublingual, buccal, intratracheal and intranasal administration forms, subcutaneous, intramuscular or intravenous administration forms and rectal administration forms. For topical application, the compounds according to the invention may be used in creams, ointments or lotions.

The dose of active principle administered per day may range from 0.1 to 1000 mg/kg via the oral, parenteral or rectal route. There may be special cases in which higher or lower doses are suitable, such doses also forming part of the invention. In usual practice, the dose which is suitable for each patient is determined by the doctor according to the mode of administration and the weight and response of the said patient.

When a solid composition in the form of tablets is prepared, the main active ingredient is mixed with a pharmaceutical excipient, such as gelatin, starch, lactose, magnesium stearate, talc, gum arabic or the like. The tablets may be coated with sucrose, a cellulose derivative or other materials. The tablets may be made by various techniques, such as direct tabletting, dry granulation, wet granulation or hot-melting.

A preparation in the form of gel capsules is obtained by mixing the active ingredient with a diluent and pouring the mixture obtained into soft or hard gel capsules.

Aqueous suspensions, isotonic saline solutions or sterile and injectable solutions which contain pharmacologically compatible dispersants and/or wetting agents, for example propylene glycol or butylene glycol, may be used for a parenteral administration.

According to another of its aspects, the present invention also relates to a method for treating the pathologies indicated above, which comprises the administration of a compound according to the invention or a pharmaceutically acceptable salt thereof.

What is claimed is:
1. A compound having formula (I)

$$\text{(I)}$$

in which:
R1 represents a hydrogen atom, a C1–C4 alkyl group, a halogen atom, a nitro group or a C1–C4 alkoxy group,
R2 and R2' represent, independently of each other, a hydrogen atom or a C1–C4 alkyl group,
X represents a nitrogen atom or a carbon atom,
n is equal to 1 or 2,
m is equal to 1 or 2,
and, when X represents a nitrogen atom:
R3 is not present or represents a C1–C4 alkyl group, and
R4 represents
a hydrogen atom,
a C1–C6 alkyl group,
a C3–C7 cycloalkyl group,
a C3–C7 heterocycloalkyl group optionally substituted with a C1–C4 alkyl group or a group —COOR, in which R represents a C1–C6 alkyl group,
a group —(CH$_2$)$_p$-heteroaryl, in which p may range from 0 to 4 and in which the heteroaryl group is chosen from pyridyl, aminopyridyl, pyrimidinyl, pyrazinyl, pyridazinyl, imidazolyl and thienyl groups, the said heteroaryl group optionally being substituted with a C1–C4 alkyl group,
a heteroaxylcarbonyl group, the heteroaryl group being chosen from furyl, pyridyl, pyrimidyl, pyrazinyl, pyridazinyl and imidazolyl groups,
a phenylcarbonyl group, the phenyl group optionally being substituted with a halogen atom,
a (C1–C6)alkylcarbonyl group,
a group —(CH$_2$)$_p$COOR in which p may range from 0 to 4 and in which R represents a C1–C6 alkyl group,
a phenylsulphonyl group optionally substituted on the phenyl nucleus with a halogen atom, a trifluoromethyl group, a C1–C4 alkyl group, a intro group or a C1–C4 alkoxy group, or
a —(CH$_2$)$_p$-phenyl group, in which p may range from 0 to 4 and in which the phenyl group is optionally substituted with one to three groups chosen, independently of each other, from: a C1–C4 alkyl group, a nitro group, an amino group, a hydroxyl group, a halogen atom, a trifluoromethyl group, a C1–C4 alkoxy group, a (C1–C4)alkoxyphenyl group, a C1–C4 alkylamino group, a C1–C4 dialkylamino group, an —NHCHO group or a group —NHCOR', in which R' represents a C1–C4 alkoxy group or a C1–C4 alkyl group, this C1–C4 alkyl group optionally being substituted with a dimethylamino group, and, when X represents a carbon atom:
R3 represents a hydrogen atom, a group —NR5R6, a group —N(R5)$_3^+$, a group —NHCOR7, a group —CONHR5, a group —COR7, an —NHCONH$_2$ group, an —OH group or a —CH$_2$OH group,
R4 represents
a hydrogen atom,
a —(CH$_2$)$_p$-phenyl group, in which p may range from 0 to 4 and in which the phenyl group is optionally substituted with one to three groups chosen, independently of each other, from: a C1–C4 alkyl group, a nitro group, an amino group, a halogen atom, a trifluoromethyl group or a C1–C4 alkoxy group,
a —(CH$_2$)$_p$-heteroaryl group, in which p may range from 0 to 4 and in which the heteroaryl group is chosen from a pyridyl group, an aminopyridyl group, a pyrimidinyl group, a pyrazinyl group or a pyridazinyl group, or
a group —(CH$_2$)$_t$NR7R8, in which t is equal to 0 or 1,
R5 and R6 represent, independently of each other, a hydrogen atom or a C1–C4 alkyl group, and
R7 and R8 represent, independently of each other, a C1–C4 alkyl or C1–C4 alkoxy group or together form a saturated 5- to 7-membered ring optionally comprising an additional nitrogen atom, this ring optionally being substituted, on a carbon atom or on a nitrogen atom, including the nitrogen atom to which the groups R7 and R8 are attached, with a C1–C4 alkyl group or a group —COOR", in which R" represents a phenyl or (C1–C4) alkylphenyl group,
or a pharmaceutically acceptable acid addition salt thereof,
with the proviso that when R4 represents a group —NR7R8, R3 is other than —NR5R6, —NHCOR7, —NHCONH$_2$ or —OH.

2. A compound according to claim 1 wherein:
X is a nitrogen atom and R3 is not present,
R1 represents a hydrogen atom, a C1–C4 alkyl group or a C1–C4 alkoxy group,
R2 represents a hydrogen atom or a C1–C4 alkyl group,
R2' represents a hydrogen atom,
n is equal to 1 or 2,
m is equal to 1 or 2, and
R4 represents
a hydrogen atom,
a C1–C6 alkyl group,
a C3–C7 cycloalkyl group,
a pyridyl, pyrimidinyl or pyrazinyl group, optionally substituted with a C1–C4 alkyl group,
a heteroarylcarbonyl group, the heteroaryl group being chosen from a furyl group and a pyridyl group,
a phenylcarbonyl group, the phenyl group optionally being substituted with a halogen atom,
a (C1–C6)alkylcarbonyl group,
a group —(CH$_2$)$_p$COOR in which p can range from 0 to 4 and in which R represents a C1–C6 alkyl group,
a phenylsulphonyl group,
a phenyl group substituted with one to three groups chosen, independently of each other, from: a C1–C4 alkyl group, a nitro group, an amino group, a hydroxyl group, a halogen atom, a trifluoromethyl group, a C1–C4 alkoxy group, a (C1–C4) alkoxyphenyl group, a (C1–C4)-dialkylamino group, an —NHCHO group or a group —NHCOR', in which R' represents a C1–C4 alkoxy group or a C1–C4 alkyl group, this C1–C4 alkyl group optionally being substituted with a dimethylamino group, a —(CH$_2$)$_p$-phenyl group, in which p can range from 0 to 4, a —(CH$_2$)$_p$-pyridyl group, in which p can range from 0 to 4, a —(CH$_2$)$_p$-thienyl group, in which p can range from 0 to 4, or a (C3–C7)heterocycloalkyl group optionally substituted with a C1–C4 alkyl group or a group —COOR, in which R represents a C1–C6 alkyl group, or:

X is a carbon atom and R3 is a hydrogen atom, a group —NR5R6, a group —N(R5)$_3^+$, a group —NHCOR7, a group —CONHR5, an —NHCONH$_2$ group, an —OH group or a —CH$_2$OH group, R1 represents a hydrogen atom, R2 and R2' represent, independently of each other, a hydrogen atom or a C1–C4 alkyl group, n is equal to 1 or 2, m is equal to 1, R4 represents a hydrogen atom, a benzyl group, a phenyl group optionally substituted with one to three groups chosen, independently of each other, from: a C1–C4 alkyl group, a nitro group, an amino group, a halogen atom, a trifluoromethyl group or a C1–C4 alkoxy group, a heteroaryl group chosen from an imidazolyl group, optionally substituted with a C1–C4 alkyl group, or a pyridyl group, or a group —NR7R8, R5 and R6 represent, independently of each other, a hydrogen atom or a C1–C4 alkyl group, and R7 and R8 represent, independently of each other, a C1–C4 alkyl or C1–C4 alkoxy group, or together form a saturated 5- to 7-membered ring optionally comprising an additional nitrogen atom, this ring optionally being substituted, on a carbon atom or a nitrogen atom, including the nitrogen atom to which the groups R7 and R8 are attached to form a quaternary ammonium, with a C1–C4 alkyl group or a group —COOR", in which R" represents a phenyl or (C1–C4)alkylphenyl group.

3. A compound according to claim 2 wherein:

X is a nitrogen atom and R3 is not present,

R1 represents a hydrogen atom, a methyl group or a methoxy group,

R2 represents a hydrogen atom or a methyl group,

R2' represents a hydrogen atom, n is equal to 1 or 2, m is equal to 1 or 2, and

R3 represents a hydrogen atom, to give compounds of formula (I) comprising a quaternary ammonium, or alternatively does not exist, to give compounds of formula (I) comprising a secondary or tertiary amine, R4 represents a hydrogen atom, a C1–C4 alkyl group, a C6–C7 cycloalkyl group, a pyridyl, pyrimidinyl or pyrazinyl group, optionally substituted with a C1–C4 alkyl group, a heteroarylcarbonyl group, the heteroaryl group being chosen from a furyl group and a pyridyl group, a phenylcarbonyl group, the phenyl group optionally being substituted with a halogen atom, a (C3–C5)alkylcarbonyl group, a group —(CH$_2$)$_p$COOR in which p is equal to 0 or 1 and in which R represents a C1–C4 alkyl group, a phenylsulphonyl group, a phenyl group substituted with one to three groups chosen, independently of each other, from: a methyl group, a nitro group, an amino group, a hydroxyl group, a halogen atom, a trifluoromethyl group, a methoxy group, a (C1–C4)alkoxyphenyl group, a dimethylamino group, an —NHCHO group or a group —NHCOR', in which R' represents a C1–C4 alkoxy group or a C1–C4 alkyl group, this C1–C4 alkyl group optionally being substituted with a dimethylamino group, a —(CH$_2$)$_p$-phenyl group, in which p is equal to 1, 2, 3 or 4, a —(CH$_2$)$_p$-pyridyl group, in which p can range from 1 to 3, a —(CH$_2$)$_p$-thienyl group, in which p is equal to 2, or a C6–C7 heterocycloalkyl group optionally substituted with a methyl group or a group —COOR, in which R represents a C1–C4 alkyl group, or X is a carbon atom R3 is a hydrogen atom, a group —NR5R6, an —N(CH$_3$)$_3^+$ group, a group —NHCOR7, a group —CONHR5, an —NHCONH$_2$ group, an —OH group or a —CH$_2$OH group, R1 represents a hydrogen atom, R2 and R2' represent, independently of each other, a hydrogen atom or a methyl group, n is equal to 1 or 2, m is equal to 1, R4 represents a hydrogen atom, a benzyl group, a phenyl group optionally substituted with one to three groups chosen, independently of each other, from a halogen atom and a trifluoromethyl group, a heteroaryl group chosen from an imidazolyl group, optionally substituted with a methyl group, or a pyridyl group, or a group —NR7R8, R5 and R6 represent, independently of each other, a hydrogen atom or a C1–C4 alkyl group, and R7 and R8 represent, independently of each other, a C1–C4 alkyl group or together form a saturated 5- to 7-membered ring optionally comprising an additional nitrogen atom, this ring optionally being substituted, on a carbon atom or on a nitrogen atom, including the nitrogen atom to which the groups R7 and R8 are attached to form a quaternary ammonium, with a methyl group or a group —COOR", in which R" represents a (C1–C4)alkylphenyl group.

4. A process for preparing a compound according to claim 1 wherein a compound of formula (II):

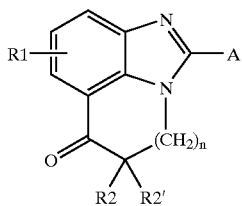

in which R1, R2, R2' and n are as defined in claim 1 and A represents a leaving group, is reacted with an amine of formula (III):

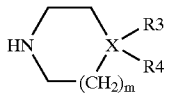

in which X, R3, R4 and m are as defined in claim 1, in a solvent.

5. A process according to claim 4 wherein the solvent is an alcohol, an ether, or a hydrocarbon.

6. A process according to claim 5 carried out in the presence of a base.

7. A process according to claim 5 carried out in the presence of a palladium-based or nickel-based catalyst.

8. A process according to claim 6 carried out in the presence of an alkali metal halide.

9. A compound having formula (II):

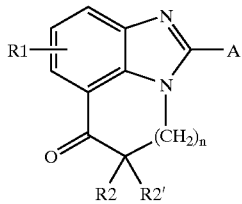

wherein
R1 is hydrogen, C1–C4 alkyl, halogen, nitro or C1–C4 alkoxy,
R2 and R2' are independently hydrogen or C1–C4 alkyl,
n is 1 or 2, and
A is a leaving group.

10. A compound according to claim 9 wherein A is halogen.

11. A pharmaceutical composition which comprises a compound according to claim 1 together with a pharmaceutically acceptable excipient.

12. A pharmaceutical composition which comprises a compound according to claim 2 together with a pharmaceutically acceptable excipient.

13. A pharmaceutical composition which comprises a compound according to claim 3 together with a pharmaceutically acceptable excipient.

14. A compound according to claim 3 wherein X is nitrogen and R3 is not present.

15. A compound according to claim 14 having the formula

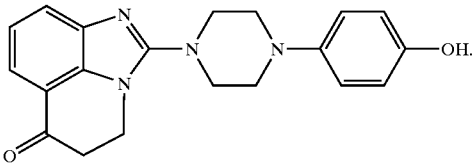

16. A compound according to claim 14 having the formula

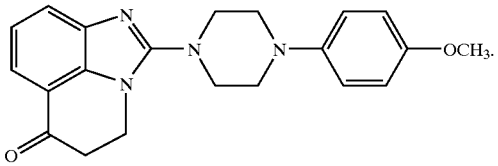

17. A compound according to claim 3 wherein X is carbon and $R_3$ is hydrogen, $NR_5R_6$, $N(CH_3)_3^+$ $NHCOR7$, $CONHR_5$, $NHCONH_2$, OH or $CH_2OH$.

18. A compound according to claim 17 wherein $R_3$ is $NR_5R_6$.

19. A compound according to claim 18 having the formula

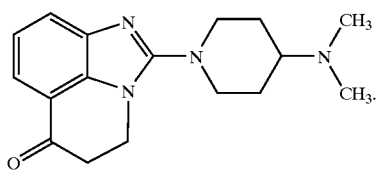

20. A pharmaceutical composition comprising a compound according to claim 14 together with a pharmaceutically acceptable excipient.

21. A pharmaceutical composition comprising a compound according to claim 15 together with a pharmaceutically acceptable excipient.

22. A pharmaceutical composition comprising a compound according to claim 16 together with a pharmaceutically acceptable excipient.

23. A pharmaceutical composition comprising a compound according to claim 17 together with a pharmaceutically acceptable excipient.

24. A pharmaceutical composition comprising a compound according to claim 18 together with a pharmaceutically acceptable excipient.

25. A pharmaceutical composition comprising a compound according to claim 19 together with a pharmaceutically acceptable excipient.

* * * * *